United States Patent [19]
Dean et al.

[11] Patent Number: 5,849,261
[45] Date of Patent: Dec. 15, 1998

[54] RADIOLABELED VASOACTIVE INTESTINAL PEPTIDES FOR DIAGNOSIS AND THERAPY

[75] Inventors: Richard T. Dean; Daniel A. Pearson; John Lister-James, all of Bedford; Edgar R. Civitello, Bradford, all of N.H.

[73] Assignee: Diatide, Inc., Londonderry, N.H.

[21] Appl. No.: 414,424

[22] Filed: Mar. 31, 1995

Related U.S. Application Data

[63] Continuation-in-part of Ser. No. 871,282, Apr. 30, 1992, Ser. No. 253,973, Jun. 3, 1994, Ser. No. 236,402, May 2, 1994, and Ser. No. 264,176, Jun. 22, 1994, abandoned, which is a continuation of Ser. No. 653,012, Feb. 8, 1991, abandoned, said Ser. No. 253,973, Ser. No. 236,402, each is a continuation-in-part of Ser. No.807,062, Nov. 27, 1991, Pat. No. 5,443,815.

[51] Int. Cl.$^6$ .......................... A61K 51/00; A61M 36/14
[52] U.S. Cl. ...................... 424/1.69; 424/1.11; 424/1.65; 424/9.1; 534/14; 534/10; 530/300; 530/311; 530/315; 530/324
[58] Field of Search .................................. 424/1.11, 1.69, 424/9.1, 1.65, 9.3, 9.4; 206/569, 223, 570; 534/10, 14–16, 9.5, 7, 11–13; 530/300, 324–330, 333, 334, 338, 311, 315, 317

[56] References Cited

U.S. PATENT DOCUMENTS

| | | |
|---|---|---|
| 4,434,151 | 2/1984 | Byrne et al. . |
| 4,444,690 | 4/1984 | Fritzberg et al. . |
| 4,472,509 | 9/1984 | Gansow et al. . |
| 4,493,523 | 1/1985 | Stavrianopoulos . |
| 4,571,430 | 2/1986 | Byrne et al. . |
| 4,575,556 | 3/1986 | Byrne et al. . |
| 4,668,503 | 5/1987 | Hnatowich et al. . |
| 4,732,684 | 3/1988 | Tolman et al. . |
| 4,832,940 | 5/1989 | Ege et al. . |
| 4,861,869 | 8/1989 | Nicolotti et al. . |
| 4,925,650 | 5/1990 | Nosco et al. . |
| 4,965,392 | 10/1990 | Fritzberg et al. . |
| 4,986,979 | 1/1991 | Morgan et al. . |
| 5,061,641 | 10/1991 | Schochat et al. . |
| 5,091,514 | 2/1992 | Fritzberg et al. . |
| 5,112,953 | 5/1992 | Gustavson et al. . |
| 5,175,257 | 12/1992 | Kasina et al. . |
| 5,180,816 | 1/1993 | Dean et al. . |
| 5,225,180 | 7/1993 | Dean et al. . |
| 5,234,907 | 8/1993 | Bolin .......................................... 514/12 |
| 5,248,764 | 9/1993 | Flanagan et al. . |
| 5,273,963 | 12/1993 | Moody ....................................... 514/12 |
| 5,428,015 | 6/1995 | Kurono et al. ........................... 530/324 |
| 5,443,815 | 8/1995 | Dean et al. ............................... 424/1.69 |
| 5,746,996 | 5/1998 | Govindan et al. ...................... 424/1.69 |

FOREIGN PATENT DOCUMENTS

| | | |
|---|---|---|
| 135160 A2 | 3/1985 | European Pat. Off. . |
| 237150 A2 | 3/1986 | European Pat. Off. . |
| 188256 A1 | 7/1986 | European Pat. Off. . |
| 271806 A2 | 12/1986 | European Pat. Off. . |
| 403243 A1 | 12/1990 | European Pat. Off. . |
| 412012 A1 | 2/1991 | European Pat. Off. . |
| 483704 A1 | 5/1992 | European Pat. Off. . |

(List continued on next page.)

OTHER PUBLICATIONS

Said and Mutt, 1970, *Science* 169: 1217–1218.
Boissard et al., 1986, *Cancer Res.* 46: 4406–4413.
El Battari et al., 1988, *J. Biol. Chem.* 263: 17685–17689.
Shaffer et al., 1987, *Peptides* 8: 1101–1106.
Svoboda et al., 1988, *Eur. J. Biochem.* 176: 707–713.
Gespach et al., 1988, *Cancer Res.* 48: 5079–5083.
Muller et al., 1989, *J. Biol. Chem.* 264:3647–3650.
Lee et al., 1990, *Peptides* 11: 1205–1210.
Park et al., 1990, *Cancer Res.* 50: 2773–2780.
Bellan et al., 1992, *Exp. Cell Res.* 200: 34–40.
Moody et al., 1993, *Proc. Natl. Acad. Sci. USA* 90: 4345–4349.
Virgolini et al., 1994, *Cancer Res.* 54: 690–700.
Larson, 1991, *J. Nucl. Med.* 32: 1189–1191.
Davison et al., 1981, *Inorg. Chem.* 20: 1629–1632.
Fritzberg et al., 1982, *J. Nucl. Med.* 23: 592–598.
Byrne et al., 1983, *J. Nucl. Med.* 24: P126.
Bryson et al., 1988, *Inorg. Chem.* 27: 2154–2161.
Misra et al., 1989, *Tet. Lett.* 30: 1885–1888.
Kwekkeboom et al., 1991, *J. Nucl. Med.* 32: 981 Abstract #305.
Rhodes, 1974, *Sem. Nucl. Med.* 4: 281–293.
Khaw et al., 1982, *J. Nucl. Med.* 23: 1011–1019.
Schwartz et al., 1991, *Bioconjugate Chem.* 2: 333.
Babich et al., 1993, *J. Nucl. Med.* 34: 1964–1974.
Schatten et al., 1991, *Lanccet* 6: 395–396.
Carstairs and Barnes, 1986, *J. Pharmacol. Exp. Ther.* 239: 249–255.
Virgolini et al., 1990, *Brit. J. Cancer* 12: 849–861.

*Primary Examiner*—Gary E. Hollinden
*Assistant Examiner*—Dameron Jones
*Attorney, Agent, or Firm*—Patricia A. McDaniels; Kevin E. Noonan

[57] ABSTRACT

This invention relates to radiotherapeutic reagents and peptides, radiodiagnostic reagents and peptides, and methods for producing labeled radiodiagnostic and radiotherapeutic agents. Specifically, the invention relates to VIP receptor binding peptides, derivatives and analogues of VIP, and embodiments of such peptides radiolabeled with a radioisotope, as well as methods and kits for making, radiolabeling and using such peptides for radiodiagnostic and radiotherapeutic purposes. The invention specifically relates to VIP receptor binding peptide derivatives and analogues of VIP radiolabeled with technetium-99m and uses thereof as scintigraphic imaging agents. The invention also specifically relates to VIP receptor binding peptide derivatives and analogues of VIP radiolabeled with cytotoxic radioisotopes such as rhenium-186 ($^{186}$Re) and rhenium-188 ($^{188}$Re) for use as radiotherapeutic agents. Methods and kits for making, radiolabeling and using such peptides diagnostically and therapeutically in a mammalian body are also provided.

37 Claims, No Drawings

FOREIGN PATENT DOCUMENTS

| | | |
|---|---|---|
| WO 85/03231 | 8/1985 | WIPO . |
| WO 88/07382 | 10/1988 | WIPO . |
| WO 89/00051 | 1/1989 | WIPO . |
| WO 89/07456 | 8/1989 | WIPO . |
| WO 89/10760 | 11/1989 | WIPO . |
| WO 89/12625 | 12/1989 | WIPO . |
| WO 90/06323 | 6/1990 | WIPO . |
| WO 90/06949 | 6/1990 | WIPO . |
| WO 90/10463 | 9/1990 | WIPO . |
| WO 91/01144 | 2/1991 | WIPO . |
| WO 91/09876 | 7/1991 | WIPO . |
| WO 91/17173 | 11/1991 | WIPO . |
| 9213572 | 8/1992 | WIPO . |
| WO 92/13572 | 8/1992 | WIPO . |
| WO 92/21383 | 12/1992 | WIPO . |
| 9310747 | 6/1993 | WIPO . |
| WO 93/10747 | 6/1993 | WIPO . |
| WO 93/12819 | 7/1993 | WIPO . |
| WO 93/13317 | 7/1993 | WIPO . |
| WO 93/15770 | 8/1993 | WIPO . |
| 9317719 | 9/1993 | WIPO . |
| WO 93/17719 | 9/1993 | WIPO . |
| WO 93/21151 | 10/1993 | WIPO . |
| 9321962 | 11/1993 | WIPO . |
| 9323085 | 11/1993 | WIPO . |
| WO 93/21962 | 11/1993 | WIPO . |
| WO 93/23085 | 11/1993 | WIPO . |
| 9325244 | 12/1993 | WIPO . |
| WO 93/25244 | 12/1993 | WIPO . |
| 9400489 | 1/1994 | WIPO . |
| WO 94/07918 | 4/1994 | WIPO . |
| 9419024 | 9/1994 | WIPO . |
| WO 94/19024 | 9/1994 | WIPO . |
| 9423758 | 10/1994 | WIPO . |
| 9428942 | 12/1994 | WIPO . |
| 9500553 | 1/1995 | WIPO . |
| WO 95/00553 | 1/1995 | WIPO . |
| 9503330 | 2/1995 | WIPO . |
| 9630055 | 10/1996 | WIPO . |

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 28
        ( D ) OTHER INFORMATION: /label=Amide
            / note= "The carboxyl terminus is modified to an amide"

( x i ) SEQUENCE DESCRIPTION: SEQ ID NO:1:

```
His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
                20                  25
```

( 2 ) INFORMATION FOR SEQ ID NO:2:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 31
    ( D ) OTHER INFORMATION: /label=Amide
        / note= "The carboxyl terminus is modified to an amide"

( x i ) SEQUENCE DESCRIPTION: SEQ ID NO:2:

| His | Ser | Asp | Ala | Val | Phe | Thr | Asp | Asn | Tyr | Thr | Arg | Leu | Arg | Lys | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Met | Ala | Val | Lys | Lys | Tyr | Leu | Asn | Ser | Ile | Leu | Asn | Gly | Gly | Cys |
|-----|-----|-----|-----|-----|-----|-----|-----|-----|-----|-----|-----|-----|-----|-----|
|     |     |     | 20  |     |     |     |     | 25  |     |     |     |     | 30  |     |

( 2 ) INFORMATION FOR SEQ ID NO:3:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 31
    ( D ) OTHER INFORMATION: /label=Amide
        / note= "The carboxyl terminus is modified to an amide"

( x i ) SEQUENCE DESCRIPTION: SEQ ID NO:3:

| Ala | Gly | Cys | His | Ser | Asp | Ala | Val | Phe | Thr | Asp | Asn | Tyr | Thr | Arg | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Lys | Gln | Met | Ala | Val | Lys | Lys | Tyr | Leu | Asn | Ser | Ile | Leu | Asn |
|-----|-----|-----|-----|-----|-----|-----|-----|-----|-----|-----|-----|-----|-----|-----|
|     |     |     | 20  |     |     |     |     | 25  |     |     |     |     | 30  |     |

( 2 ) INFORMATION FOR SEQ ID NO:4:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 29
    ( D ) OTHER INFORMATION: /label=Amide
        / note= "The carboxyl terminus is modified to an amide"

( i x ) FEATURE:
    ( A ) NAME/KEY: Modified-site
    ( B ) LOCATION: 29
    ( D ) OTHER INFORMATION: /label=BAT
        / note= "The side chain sulfur atom of the carboxyl
        terminal cysteine residue is covalently linked to a
        BAT radiolabel binding moiety"

( x i ) SEQUENCE DESCRIPTION: SEQ ID NO:4:

| His | Ser | Asp | Ala | Val | Phe | Thr | Asp | Asn | Tyr | Thr | Arg | Leu | Arg | Lys | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Met | Ala | Val | Lys | Lys | Tyr | Leu | Asn | Ser | Ile | Leu | Asn | Cys |
|-----|-----|-----|-----|-----|-----|-----|-----|-----|-----|-----|-----|-----|
|     |     |     | 20  |     |     |     |     | 25  |     |     |     |     |

( 2 ) INFORMATION FOR SEQ ID NO:5:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 27
        ( D ) OTHER INFORMATION: /label=Amide
            / note= "The carboxyl terminus is modified to an
            amide"

( x i ) SEQUENCE DESCRIPTION: SEQ ID NO:5:

Ser Asp Ala Val Phe Thr Asp Asn Tyr Thr Arg Leu Arg Lys Gln Met
1               5                   10                  15

Ala Val Lys Lys Tyr Leu Asn Ser Ile Leu Asn
            20                  25

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 20
        ( D ) OTHER INFORMATION: /label=Amide
            / note= "The carboxyl terminus is modified to an
            amide"

( x i ) SEQUENCE DESCRIPTION: SEQ ID NO:6:

Asn Tyr Thr Arg Leu Arg Lys Gln Met Ala Val Lys Lys Thr Leu Asn
1               5                   10                  15

Ser Ile Leu Asn
            20

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 14
        ( D ) OTHER INFORMATION: /label=Amide
            / note= "The carboxyl terminus is modified to an
            amide"

( x i ) SEQUENCE DESCRIPTION: SEQ ID NO:7:

Lys Gln Met Ala Val Lys Lys Thr Leu Asn Ser Ile Leu Asn
1               5                   10

RADIOLABELED VASOACTIVE INTESTINAL PEPTIDES FOR DIAGNOSIS AND THERAPY

This application is a continuation-in-part of U.S. patent application Ser. No. 08/264,176, filed Jun. 22, 1994 and now abandoned; which is a continuation of U.S. patent application Ser. No. 07/653,012, filed Feb. 8, 1991 and now abandoned; this application is also a continuation-in-part of U.S. patent application Ser. No. 08/253,973, filed Jun. 3, 1994 and of U.S. patent application Ser. No. 08/236,402, filed May 2, 1994, said U.S. patent application Ser. Nos. 081253,973 and 08/236,402 being continuations-in-part of U.S. patent application Ser. No. 07/802,062, filed Nov. 27, 1991 and now U.S. Pat. No 5,443,815; this application is also a continuation-in-part of U.S. patent application Ser. No. 07/871,282, filed Apr. 30, 1992.

BACKGROUND OF THE INVENTION

1. Field of the Invention

This invention relates to radiotherapeutic agents and peptides, radiodiagnostic agents and peptides, and methods for producing such labeled radiodiagnostic and radiotherapeutic agents. Specifically, the invention relates to vasoactive intestinal peptide (VIP) receptor binding peptides and derivatives and analogues thereof, and embodiments of such peptides labeled with gamma-radiation emitting isotopes such as technetium-99m (Tc-99m), as well as methods and kits for making, radiolabeling and using such peptides to image sites in a mammalian body. The invention also relates to receptor binding VIP peptides and derivatives and analogues thereof, labeled with cytotoxic radioisotopes such as rhenium-186 ($^{186}$Re) and rhenium-188 ($^{188}$Re), and methods and kits for making, radiolabeling and using such peptides therapeutically in a mammalian body.

2. Description of the Prior Art

Vasoactive intestinal peptide (VIP) is a 28 amino acid peptide that was first isolated from hog upper small intestine (Said and Mutt, 1970, Science 169: 1217–1218). This peptide belongs to a family of structurally-related, small peptides that includes helodermin, secretin, the somatostatins, and glucagon. The peptide has the formula:

Formula I

HSDAVFTDNYTRLRKQMAVKKYLNSILN. amide (SEQ.ID NO.1) (where single-letter abbreviations for amino acids can be found in Zubay, Biochemistry 2d ed., 1988, MacMillan Publishing: New York, p. 33).

The biological effects of VIP are mediated by the activation of membrane-bound receptor proteins that are coupled to the intracellular cyclic adenosine monophosphate signalling system. VIP regulates a variety of different biological activities in tissues and organs. It modulates cellular metabolic activities and regulates exocrine and endocrine secretions. It also induces relaxation of smooth muscle and causes vasodilatory effects. VIP is also involved in the regulation of cellular proliferation and survival in a number of different cell types, including keratinocytes, smooth muscle cells, sympathetic neuroblasts, hippocampal cells and, in vitro, NIH 3T3 cells.

VIP receptors are widely distributed throughout the gastrointestinal tract and are also found in various other cell types. Large numbers of VIP receptors are expressed in tumor cells of adenocarcinomas, breast cancers, melanomas, neuroblastomas and pancreatic carcinomas. In fact, expression of high affinity binding sites for VIP (comprising the VIP receptor protein) is a marker for these tumor cells. Specific binding of VIP to these cells can be exploited as a marker to locate and identify such tumor cells in vivo.

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. A number of factors must be considered for optimal radioimaging in humans. To maximize the efficiency of detection, a radionuclide that emits gamma energy in the 200 to 200keV range is preferred. To minimize the absorbed radiation dose to the patient, the physical half-life of the radionuclide must be as short as the imaging procedure will allow. To allow for examinations to be performed on any day and at any time of the day, it is advantageous to have a source of the radionuclide always available at the clinical site.

Methods for radioiodinating VIP analogues at tyrosine residues in the VIP sequence (Tyr$^{10}$ or Tyr$^{22}$) using $^{123}$I or $^{125}$I are known in the prior art. These radioiodinated species have also been used to assess VIP binding to receptors on tumor cells.

Boissard et al., 1986, Cancer Res. 46: 4406–4413 describe radioiodination of VIP and binding to human colon adenocarcinoma cells.

El Battari et al., 1988, J. Biol. Chem. 263: 17685–17689 describe radioiodination of VIP and binding to human colon adenocarcinoma cells.

Shaffer et al., 1987, Peptides 8: 1101–1106 disclose radioiodination of VIP and binding to human small cell and non-small cell carcinoma cells.

Svoboda et al., 1988, Eur. J. Biochem. 176: 707–713 describe radioiodination of VIP and binding to rat transformed pancreatic acinar cells.

Gespach et al., 1988, Cancer Res. 48: 5079–5083 disclose radioiodination of VIP and binding to human breast cancer cells.

Muller et al., 1989, J. Biol. Chem. 264: 3647–3650 disclose radioiodination of VIP and binding to human neuroblastoma cells.

Lee et al., 1990, Peptides 11: 1205–1210 disclose radioiodination of VIP and binding to human small cell and non-small cell carcinoma cells.

Park et al., 1990, Cancer Res. 50: 2773–2780 describe radioiodination of VIP and binding to human gastric cancer cells.

Bellan et al., 1992, Exp. Cell Res. 200: 34–40 disclose radioiodination of VIP and binding to human melanoma cells.

Moody et al., 1993, Proc. Natl. Acad. Sci. USA 90: 4345–4349 disclose radioiodination of VIP and binding to non-small cell lung carcinoma cells.

Virgolini et al., 1994, Cancer Res. 54: 690–700 describe radioiodination of VIP and binding to primary tumors and tumor cell lines.

Methods for radioiodinating VIP analogues at $Y^{10}$ or $Y^{22}$ using $^{131}$I are known in the prior art.

Hassan et al., 1994, Nucl. Med. Biol. 21: 865–872 disclose radioiodination of VIP and in vivo distribution of radiolabel in a rat by scintigraphy.

These methods have application for enabling detection of tumor cells in vivo by radioimaging, particularly radioscintigraphy. VIP is a useful marker for such radioimaging, because many different tumor cells express a high affinity binding site for VIP (the VIP receptor protein). However, radioiodinated peptides have significant commercial disadvantages. $^{123}$I is both expensive and in limited supply. Also, approved radioiodinated radiopharmaceuticals normally cannot be prepared at the clinical site.

Tc-99m is a preferred radionuclide because it emits gamma radiation at 140 keV, it has a physical half-life of 6 hours, and it is readily available on-site using a molybdenum-99/technetium-99m generator. Other radionuclides used in the prior art are less advantageous than Tc-99m. This can be because the physical half-lives of such radionuclides are longer, resulting in a greater amount of absorbed radiation dose to the patient (e.g., indium-111). Alternatively, the gamma radiation energies of such alternate radionuclides are significantly lower (e.g., iodine-125) or higher (e.g., iodine-131) than Tc-99m and are thereby inappropriate for quality scintigraphic imaging. Lastly, many disadvantageous radionuclides cannot be produced using an on-site generator.

Tc-99m is a transition metal that is advantageously chelated by a metal complexing moiety. Radiolabel complexing moieties capable of binding Tc-99m can be covalently linked to various specific binding compounds to provide a means for radiolabeling such specific binding compounds. This is because the most commonly available chemical species of Tc-99m, pertechnetate ($TcO_4^-$), cannot bind directly to most specific binding compounds strongly enough to be useful as a radiopharnaceutical. Complexing of Tc-99m with such radiolabel complexing moieties typically entails chemical reduction of the pertechnetate using a reducing agent such as stannous chloride.

Although Tc-99m is the preferred radionuclide for scintigraphic imaging, it has not been widely used for labeling peptides (see Lamberts, 1991, *J. Nucl. Med.* 32: 1189–1191). This is because methods known in the prior art for labeling larger protein molecules (i.e., >10,000 daltons in size) with Tc-99m are not suitable for labeling peptides (having a molecular size less than 10,000 daltons). Consequently, it is necessary to radiolabel most peptides by covalently attaching a radionuclide chelating moiety to the peptide, so that the chelator is incorporated site-selectively at a position in the peptide that will not interfere with the specific binding properties of the peptide.

Methods for labeling peptides with Tc-99m are disclosed in co-owned U.S. Pat. No. 5,225,180 and in co-pending U.S. patent applications Ser. Nos. 07/653,012, 07/807,062, 07/851,074, 07/871,282, 07/886,752, 07/893,981, 07/902,935, 07/955,466, 07/977,628, 08/019,864, 08/044,825 and 08/073,577, 08/092,355, 08/095,760, 08/210,822, and PCT International Applications PCT/US92/00757, PCT/US92/10716, PCT/US93/02320, PCT/US93/03687, PCT/US93/04794, PCT/US93/05372, PCT/US93/06029, PCT/US93/09387, and PCT/US94/01894, which are hereby incorporated by reference.

Methods for preparing Tc-99m complexes are known in the art.

Byrne et al., U.S. Pat. Nos. 4,434,151, 4,575,556 and 4,571,430 describe homocysteine thiolactone-derived bifunctional chelating agents.

Fritzberg, U.S. Pat. No. 4,444,690 describes a series of technetium-chelating agents based on 2,3-bis(mercaptoacetamido) propanoate.

Nosco et al., U.S. Pat. No. 4,925,650 describe Tc-99m chelating complexes.

Kondo et al., European Patent Application, Publication No. 483704 A1 disclose a process for preparing a Tc-99m complex with a mercapto-Gly-Gly-Gly moiety.

European Patent Application No. 84109831.2 describes bisamido, bisthiol Tc-99m ligands and salts thereof as renal function monitoring agents.

Davison et al., 1981, *Inorg. Chem.* 20: 1629–1632 disclose oxotechnetium chelate complexes.

Fritzberg et al., 1982, *J. Nucl. Med.* 23: 592–598 disclose a Tc-99m chelating agent based on N, N'-bis(mercaptoacetyl)-2,3-diaminopropanoate.

Byrne et al., 1983, *J. Nucl. Med.* 24: P126 describe homocystine-containing Tc-99m chelating agents.

Bryson et al., 1988, *Inorg. Chem.* 27: 2154–2161 describe neutral complexes of technetium-99 which are unstable to excess ligand.

Misra et al., 1989 *Tet. Lett.* 30: 1885–1888 describe bisamine bisthiol compounds for radiolabeling purposes.

The use of chelating agents for radiolabeling specific-binding compounds is known in the art.

Gansow et al., U.S. Pat. No. 4,472,509 teach methods of manufacturing and purifying Tc-99m chelate-conjugated monoclonal antibodies.

Stavrianopoulos, U.S. Pat. No. 4,943,523 teach detectable molecules comprising metal chelating moieties.

Fritzberg et al., European Patent Application No. 86100360.6 describe dithiol, diamino, or diamidocarboxylic acid or amine complexes useful for making technetium-labeled imaging agents.

Albert et al., UK Patent Application 8927255.3 disclose radioimaging using somatostatin derivatives such as octreotide labeled with $^{111}$In via a chelating group bound to the amino-terminus.

Albert et al., European Patent Application No. WO91/01144 disclose radioimaging using radiolabeled peptides related to growth factors, hormones, interferons and cytokines and comprised of a specific recognition peptide covalently linked to a radionuclide chelating group.

Fischman et al., International Patent Application, Publication No. WO93/13317 disclose chemotactic peptides attached to chelating moieties.

Kwekkeboom et al., 1991, J. Nucl. Med. 32: 981 Abstract #305 relates to radiolabeling somatostatin analogues with [111]In.

Albert et al., 1991, Abstract LM10, 12th American Peptide Symposium: 1991 describe uses for $^{111}$In-labeled diethylene-triaminopentaacetic acid-derivatized somatostatin analogues.

Cox et al., 1991, Abstract, 7th International Symposium on Radiopharmacology, p. 16, disclose the use of, Tc-99m-, [131]I- and $^{111}$In-labeled somatostatin analogues in radiolocalization of endocrine tumors in vivo by scintigraphy.

Methods for labeling certain specific-binding compounds with Tc-99m are known in the prior art.

Hnatowich, U.S. Pat. No. 4,668,503 describe Tc-99m protein radiolabeling.

Tolman, U.S. Pat. No. 4,732,684 describe conjugation of targeting molecules and fragments of metallothionein.

Nicolotti et al., U.S. Pat. No. 4,861,869 describe bifunctional coupling agents useful in forming conjugates with biological molecules such as antibodies.

Fritzberg et al., U.S. Pat. No. 4,965,392 describe various S-protected mercaptoacetylglycylglycine-based chelators for labeling proteins.

Schochat et al., U.S. Pat. No. 5,061,641 disclose direct radiolabeling of proteins comprised of at least one "pendent" sulfhydryl group.

Fritzberg et al., U.S. Pat. No. 5,091,514 describe various S-protected mercaptoacetylglycylglycine-based chelators for labeling proteins.

Gustavson et al., U.S. Pat. No. 5,112,953 disclose Tc-99m chelating agents for radiolabeling proteins.

Kasina et al., U.S. Pat. No. 5,175,257 describe various combinations of targeting molecules and Tc-99m chelating groups.

Dean et al., U.S. Pat. No. 5,180,816 disclose methods for radiolabeling a protein with Tc-99m via a bifunctional chelating agent.

Sundrehagen, International Patent Application, Publication No. WO85/03231 disclose Tc-99m labeling of proteins.

Reno and Bottino, European Patent Application 87300426.1 disclose radiolabeling antibodies with Tc-99m.

Bremer et al., European Patent Application No. 87118142.6 disclose Tc-99m radiolabeling of antibody molecules.

Pak et al., European Patent Application No. WO88/07382 disclose a method for labeling antibodies with Tc-99m.

Goedemans et al., PCT Application No. WO89/07456 describe radiolabeling proteins using cyclic thiol compounds, particularly 2-iminothiolane and derivatives.

Dean et al., International Patent Application, Publication No. WO89/12625 teach bifunctional coupling agents for Tc-99m labeling of proteins.

Schoemaker et al., International Patent Application, Publication No. WO90/06323 disclose chimeric proteins comprising a metal-binding region.

Thomback et al., EPC Application No. 90402206.8 describe preparation and use of radiolabeled proteins or peptides using thiol-containing compounds, particularly 2-iminothiolane.

Gustavson et al., International Patent Application, Publication No. WO91/09876 disclose Tc-99m chelating agents for radiolabeling proteins.

Rhodes, 1974, Sem. Nucl. Med. 4: 281–293 teach the labeling of human serum albumin with technetium-99m.

Khaw et al., 1982, J. Nucl. Med. 23: 1011–1019 disclose methods for labeling biologically active macromolecules with Tc-99m.

Schwartz et al., 1991, Bioconjugate Chem. 2: 333 describe a method for labeling proteins with Tc-99m using a hydrazinonicotinamide group.

Attempts at labeling peptides have been reported in the prior art.

Ege et al., U.S. Pat. No. 4,832,940 teach radiolabeled peptides for imaging localized T-lymphocytes.

Morgan et al., U.S. Pat. No. 4,986,979 disclose methods for imaging sites of inflammation.

Flanagan et al., U.S. Pat. No. 5,248,764 describe conjugates between a radiolabel chelating moiety and atrial natiuretic factor-derived peptides.

Ranby et al., 1988, PCT/US88/02276 disclose a method for detecting fibrin deposits in an animal comprising covalently binding a radiolabeled compound to fibrin.

Lees et al., 1989, PCT/US89/01854 teach radiolabeled peptides for arterial imaging.

Morgan et al., International Patent Application, Publication No. WO90/10463 disclose methods for imaging sites of inflammation.

Flanagan et al., European Patent Application No. 90306428.5 disclose Tc-99m labeling of synthetic peptide fragments via a set of organic chelating molecules.

Stuttle, PCT Application, Publication No. WO90/15818 suggests Tc-99m labeling of RGD-containing oligopeptides.

Rodwell et al., 1991, PCT/US91/03116 disclose conjugates of "molecular recognition units" with "effector domains".

Cox, International Patent Application No. PCT/US92/04559 discloses radiolabeled somatostatin derivatives containing two cysteine residues.

Rhodes et al., International Patent Application, Publication No. WO93/12819 teach peptides comprising metal ion-binding domains.

Lyle et al, International Patent Application, Publication No. WO93/15770 disclose Tc-99m chelators and peptides labeled with Tc-99m.

Coughlin et al, International Patent Application, Publication No. WO93/21151 disclose bifunctional chelating agents comprising thiourea groups for radiolabeling targeting molecules.

Knight et al., 1990, 37th Annual Meeting of the Society of Nuclear Medicine, Abstract #209, claim thrombus imaging using Tc-99m labeled peptides.

Babich et al., 1993, *J. Nucl. Med.* 34: 1964–1974 describe Tc-99m labeled peptides comprising hydrazinonicotinamide derivatives.

VIP receptor binding peptides and radiolabeled derivatives and analogues thereof can also be used therapeutically. For these applications, cytotoxic radioisotopes are advantageous, such as rhenium-186 and rhenium-188.

There remains a need for synthetic (to make routine manufacture practicable and to ease regulatory acceptance) VIP receptor binding peptides, derivatives and analogues thereof to be used as scintigraphic agents when radiolabeled with Tc-99m for use in imaging tumors in vivo, and as radiotherapeutic agents when radiolabeled with a cytotoxic radioisotope such as rhenium-188. Small synthetic VIP receptor binding peptides and derivatives and analogues of such VIP receptor binding peptides are provided by this invention that specifically fulfill this need.

SUMMARY OF THE INVENTION

The present invention provides radiopharmaceuticals that are Tc-99m, Re-186 or Re188 labeled receptor binding VIP peptides for radiotherapeutic applications and radiodiagnostic applications, in particular scintigraphic imaging applications. The invention also provides receptor binding VIP peptide reagents comprised of the receptor binding VIP peptides, derivatives and analogues thereof, wherein such peptides are covalently linked to a chelating moiety. The invention provides such receptor binding VIP peptides, receptor binding VIP peptide reagents and radiolabeled receptor binding VIP peptide reagents that are scintigraphic imaging agents, radiodiagnostic agents and radiotherapeutic agents.

Scintigraphic imaging agents of the invention comprise receptor binding VIP peptide reagents radiolabeled with technetium-99m. Radiotherapeutic agents of the invention comprise receptor binding VIP peptide reagents radiolabeled with rhenium-186 or rhenium-188. Methods for making and using such receptor binding VIP peptides, receptor binding VIP peptide reagents and radiolabeled embodiments thereof are also provided.

The invention provides a reagent for preparing a radiopharmaceutical, wherein the reagent is a synthetic, receptor-binding vasoactive intestinal peptide (VIP) that is covalently linked to a chelating moiety capable of chelating a technetium or rhenium radiolabel. The chelating moiety is incorporated into the reagent during synthesis of the reagent. In addition, the technetium- or rhenium-labeled radiopharmaceuticals of the invention have a VIP receptor binding affinity that is not less than about one-tenth the affinity of radioiodinated native VIP. In a preferred embodiment, the invention provides scintigraphic imaging agents comprising a reagent of the invention radiolabeled with Tc-99m. In other preferred embodiments, the invention provides radiotherapeutic agents comprising a reagent of the invention radiolabeled with a cytotoxic radioisotope selected from the group consisting of rhenium-186 and rhenium-188. Complexes of the reagent and radiolabels that are Tc-99m, Re-186 or Re-188 are provided, formed by reacting a reagent of the invention with the radiolabel in the presence of a reducing agent, for example, a stannous ion. Complexes of Tc-99m, Re-186 or Re-188 with the reagents of the invention are also provided as produced by ligand exchange of a prereduced radiolabel complex.

Thus, the invention also provides scintigraphic imaging agents comprising the receptor binding VIP peptide reagents of the invention wherein the chelating moiety is stably complexed with Tc-99m.

The invention also provides radiotherapeutic agents that are the receptor binding VIP peptide reagents of the invention radiolabeled with rhenium-186 or rhenium-188.

The invention also provides pharmaceutical compositions comprising the radiolabeled VIP receptor-binding peptides of the invention in a pharmaceutically acceptable carrier.

Another aspect of the present invention provides reagents for preparing radiotherapeutic and radiodiagnostic radiopharmaceuticals, including preferably scintigraphic imaging agents. Each such reagent is comprised of a peptide that is VIP peptide, derivative or analog covalently linked to a chelating moiety.

A first aspect of the reagents provided by the invention for preparing radiolabeled agents are reagents that are each comprised of a VIP receptor-binding peptide as described above that is covalently linked to a chelating moiety having the formula:

C(pgp)$^s$-(aa)-C(pgp)$^s$ where (pgp)$^s$ is hydrogen or a thiol protecting group and (aa) is an α- or β-amino acid not comprising a thiol group. In a preferred embodiment, the amino acid is glycine. In another preferred embodiment, the agent is a scintigraphic imaging agent. In yet another preferred embodiment, the agent is a radiotherapeutic agent.

In a second embodiment, the invention provides receptor binding VIP peptide reagents capable of being radiolabeled to form radiodiagnostic and radiotherapeutic agents, each comprising a VIP peptide, derivative or analog covalently linked to a chelating moiety of formula:

A—CZ(B)—{C(R$^a$R$^b$)}$_n$—X wherein A is H, HOOC, H$_2$NOC, (peptide)-NHOC, (peptide)-OOC, R$^e$$_2$NCO, or R$^d$; B is H, SH or —NHR$^c$, —N(R$^c$)-(peptide) or R$^d$; Z is H or R$^d$; X is SH or —NHR$^c$, —N(R$^c$)-(peptide) or R$^d$; R$^a$, R$^b$, R$^c$ and R$^d$ are independently H or straight or branched chain or cyclic lower alkyl; n is 0, 1 or 2; R$^e$ is C$_1$–C$_4$ alkyl, an amino acid or a peptide comprising 2 to about 10 amino acids; and: (1) where B is —NHR$^c$ or —N(R$^c$)-(peptide), X is SH and n is 1 or 2; (2) where X is —NHR$^c$ or —N(R$^c$)-(peptide), B is SH and n is 1 or 2; (3) where B is H or R$^d$, A is HOOC, H$_2$NOC, (peptide)—NHOC, or (peptide)-OOC, X is SH and n is 0 or 1; (4) where A is H or R$^d$, then where B is SH, X is —NHR$^c$ or —N(R$^c$)-(peptide) and where X is SH, B is —NHR$^c$ or —N(R$^c$)-(peptide) and n is 1 or 2; (5) where X is H or R$^d$, A is HOOC, H$_2$NOC, (peptide)-NHOC, or (peptide)-OOC and B is SH; and (6) where Z is methyl, X is methyl, A is HOOC, H$_2$NOC, (peptide)-NHOC, or (peptide)-OOC and B is SH and n is 0; In a preferred embodiment, the agent is a scintigraphic imaging agent. In yet another preferred embodiment, the agent is a radiotherapeutic agent.

Preferred embodiments of this chelating moiety have a chemical formula that is:

R$^1$—CO-(amino acid)$^1$-(amino acid)$^2$—Z wherein (amino acid)$^1$ and (amino acid)$^2$ are each independently any primary α- or β-amino acid that does not comprise a thiol group, Z is a thiol-containing moiety that is cysteine, homocysteine, isocysteine, penicillamine, 2-mercaptoethylamine or 3-mercaptopropylamine, and R$^1$ is lower (C$^1$–C$^4$) alkyl, an amino acid or a peptide comprising 2 to 10 amino acids. When Z is cysteine, homocysteine, isocysteine or penicillamine, the carbonyl group of said moiety is covalently linked to a hydroxyl group, a NR$^3$R$^4$ group, wherein each of R$^3$ and R$^4$ are independently H or lower (C$^1$–C$^4$) alkyl, an amino acid or a peptide comprising 2 to 10 amino acids; or Y-(amino acid)$^2$-(amino acid)$^1$—NHR$^2$ wherein Y is a thiol-containing moiety that is cysteine, homocysteine, isocysteine, penicillamine, 2-mercaptoacetate or 3-mercaptopropionate, (amino acid)$^1$ and (amino acid)$^2$ are each independently any primary α- or β-amino acid that does not comprise a thiol group, and R$^2$ is H or lower (C$^1$–C$^4$) alkyl, an amino acid or a peptide comprising 2 to 10 amino acids. When Y is cysteine, homocysteine, isocysteine or penicillamine, the amino group of said moiety is covalently linked to —H, an amino acid or a peptide comprising 2 to 10 amino acids.

In particular embodiments of this aspect of the invention, the chelating moiety has a formula that is:

IIa. -(amino acid)$^1$-(amino acid)$^2$—A—CZ(B)—{C(R$^1$R$^2$)$_n$}n—X},

IIb. —A—CZ(B)—{C(R$^1$R$^2$)}$_n$—X}-(amino acid)$^1$-(amino acid)$^2$,

IIc. -(a primary α,ω- or ,β,ω-diamino acid)-(amino acid)$^1$—A—CZ(B)—{C(R$^1$R$^2$)}$_n$—X}, or IId. —A—CZ(B)—{C(R$^1$R$^2$)}$_n$—X}-(amino acid)$^1$-(a primary α,ω- or β, ω-diamino acid) wherein (amino acid)$^1$ and (amino acid)$^2$ are each independently any naturally-occurring, modified, substituted or altered α- or β-amino acid not containing a thiol group; A is H, HOOC, H$_2$NOC, (amino acid or peptide)-NHOC, (amino acid or peptide)-OOC or R$^4$; B is H, SH or —NHR$^3$, —N(R$^3$)-(amino acid or peptide) or R$^4$; Z is H or R$^4$; X is SH or —NHR$^3$,-N(R$^3$)-(amino acid Or peptide or R$^4$; R$^1$, R$^2$, R$^3$ and R$^4$ are independently H or straight or branched chain or cyclic lower alkyl; n is an integer that is either 0, 1 or 2; (peptide) is a peptide of 2 to about 10 amino acids; and: (1) where B is —NHR$^3$ or —N(R$^3$)-(amino acid or peptide), X is SH and n is 1 or 2; (2) where X is —NHR$^3$ or —N(R$^3$)-(amino acid or peptide), B is SH and n is 1 or 2; (3) where B is H or R$^4$, A is HOOC, H$_2$NOC, (amino acid or peptide)-NHOC, (amino acid or peptide)-OOC, X is SH and n is 0 or 1; (4) where A is H or R$^4$, then where B is SH, X is —NHR$^3$ or —N($^3$)-(amino acid or peptide) and where X is SH, B is —NHR$^3$ or —N(R$^3$) -(amino acid or peptide) and n is 1 or 2; (5) where X is H or R$^4$, A is HOOC, H$_2$NOC, (amino acid or peptide)-NHOC, (amino acid or peptide)-OOC and B is SH; and (6) where Z is methyl, X is methyl, A is HOOC, H$_2$NOC, (amino acid or peptide)-NHOC, (amino acid or peptide)-OOC and B is SH and n is 0;

Additional preferred embodiments include chelating moieties having the formula: -Gly-Gly-Cys-, Cys-Gly-Gly-, Gly-Gly-Cys-, -(ε-Lys)-Gly-Cys-, (δ-Orn)-Gly-Cys-, -(γ-Dab)-Gly-Cys-, and -(β-Dap)-Gly-Cys-. (In these formulae, it will be understood that ε-Lys represents a lysine residue in which the ε-amino group, rather than the typical β-amino group, is covalently linked to the carboxyl group of the adjacent amino acid to form a peptide bond; δ-Orn represents an ornithine residue in which the δ-amino group, rather than the typical α-amino group, is covalently linked to the carboxyl group of the adjacent amino acid to form a peptide bond; γ-Dab represents a 2,4-diaminobutyric acid residue in which the γ-amino group is covalently linked to the carboxyl group of the adjacent amino acid to form a peptide bond; and β-Dap represents a 1,3-diaminopropionic acid residue in which the β-amino group is covalently linked to the carboxyl group of the adjacent amino acid to form a peptide bond.)

Yet another embodiment of the invention provides receptor binding VIP peptide reagents capable of being radiolabeled with a radioisotope for imaging sites within a mammalian body or for radiotherapeutic purposes, each comprising a VIP analogue that is covalently linked to a chelating moiety that is a bisamino-bisthiol chelating moiety. The bisamino bisthiol chelating moiety in this embodiment of the invention has the formula:

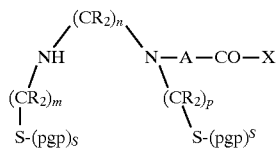

wherein each R can be independently H, $CH_3$ or $C_2H_5$; each $(pgp)^s$ can be independently a thiol protecting group or H; m, n and p are independently 2 or 3; A is linear or cyclic lower alkyl, aryl, heterocyclyl, combinations or substituted derivatives thereof; and X is peptide; or

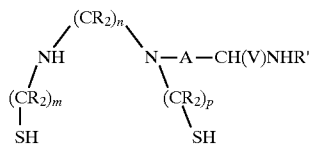

wherein each R is independently H, $CH_3$ or $C_2H_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is peptide. For purposes of this invention, chelating moieties having these structures will be referred to as "BAT" moieties. In a preferred embodiment, the agent is a scintigraphic imaging agent. In yet another preferred embodiment, the agent is a radiotherapeutic agent.

The invention also provides radiopharmaceutical agents and reagents for preparing such radiopharmaceuticals comprising a receptor binding VIP peptide, derivative or analog covalently linked to a chelating moiety selected from the group consisting of:

(i) a group having the formula:

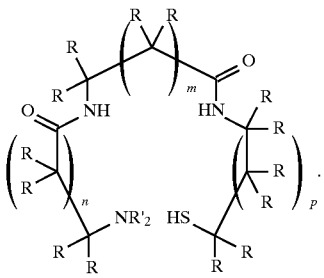

(ii) a group having the formula:

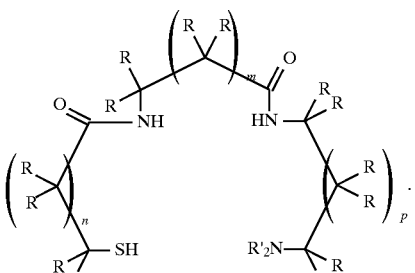

wherein n, m and p are each integers that are independently 0 or 1; each R' is independently H, lower alkyl, $C_2$–$C_4$ hydroxyalkyl, or $C_2$–$C_4$ alkoxyalkyl, and each R is independently H or R", where R" is substituted or unsubstituted lower alkyl or phenyl not comprising a thiol group, and one R or R' is L, where L is a bivalent linker moiety linking the metal chelator to the targeting moiety and wherein when one R' is L, $NR'_2$ is an amine.

In preferred embodiments, L is a $C_1$–$C_6$ linear, branched chain or cyclic alkyl group, a carboxylic ester, a carboxamide, a sulfonamide, an ether, a thioether, an amine, an alkene, an alkyne, a 1,2-, 1,3- or 1,4-linked, optionally substituted, benzene ring, or an amino acid or peptide of 2 to about 10 amino acids, or combinations thereof.

In preferred embodiments, R" is a $C_1$–$C_6$ linear, branched or cyclic alkyl group; a —$C_qOC_r$—, —$C_qNHC_r$— or —$C_qSC_r$— group, where q and r are integers each independently 1 to 5 wherein the sum of q+r is not greater than 6; ($C_1$–$C_6$) alkyl-X, where X is a hydroxyl group, a substituted amine, a guanidine, an amidine, a substituted thiol group, or a carboxylic acid, ester, phosphate, or sulfate group; a phenyl group or a phenyl group substituted with a halogen, hydroxyl, substituted amine, guanidine, amidine, substituted thiol, ether, phosphate, or sulfate group; an indole group; a $C_1$–$C_6$ heterocyclic group containing 1 to 3 nitrogen, oxygen or sulfur atoms or combinations thereof.

Preferred chelating moieties of the invention include chelators having the formula:

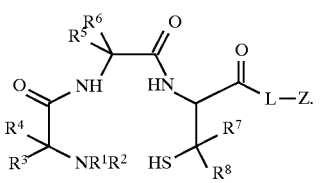

wherein $R^1$ and $R^2$ are each independently H, lower alkyl, $C_2$–$C_4$ hydroxyalkyl, or $C_2$–$C_4$ alkoxyalkyl; $R^3$, $R^4$, $R^5$ and $R^6$ are independently H, substituted or unsubstituted lower alkyl or phenyl not comprising a thiol group; $R^7$ and $R^8$ are each independently H, lower alkyl, lower hydroxyalkyl or lower alkoxyalkyl; L is a bivalent linker group and Z is a VIP peptide.

Additional preferred metal chelators of the invention include chelators of formula:

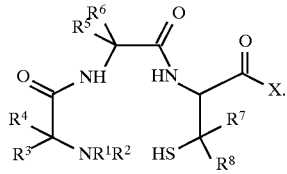

IV wherein $R^1$ and $R^2$ are each independently H, lower allyl, $C_2$–$C_4$ hydroxyalkyl, or $C_2$–$C_4$ alkoxyalkyl; $R^3$, $R^4$, $R^5$ and $R^6$ are independently H, substituted or unsubstituted lower alkyl or phenyl not comprising a thiol group, and one of $R^3$, $R^4$, $R^5$ or $R^6$ is Z—L—HN(CH$_2$)$_n$—, where L is a bivalent linker group, Z is a targeting moiety, and n is an integer from 1 to 6; $R^7$ and $R^8$ are each independently H, lower alkyl, lower hydroxyalkyl or lower alkoxyalkyl; and X is an amino group, a substituted amino group or —NR$^1$-Y, where Y is an amino acid, an amino acid amide, or a peptide comprising from 2 to 10 amino acids.

More preferred metal chelators of the invention include chelators having the formula:

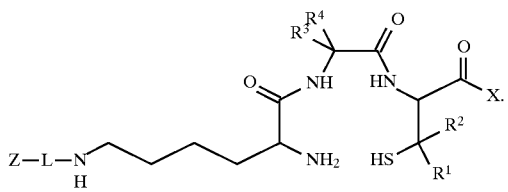

V wherein $R^1$ and $R^2$ are each independently H, lower alkyl, lower hydroxyalkyl, or lower alkenylalkyl; $R^3$ and $R^4$ are independently H, substituted or unsubstituted lower allyl or phenyl not comprising a thiol group; n is an integer from 1 to 6; L is a bivalent linker group; and Z is a VIP peptide moiety.

Additional more preferred chelating moieties include chelators of formula:

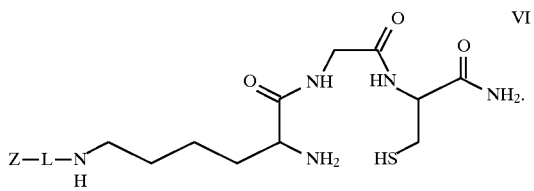

VI wherein L is a bivalent linker group and Z is a VIP peptide moiety.

Most preferred chelating moieties of the invention include chelators having the following formulae:

(amino acid)$^1$-(amino acid)$^2$-cysteine-,
(amino acid)$^1$-(amino acid)$^2$-isocysteine-,
(amino acid)$^1$-(amino acid)$^2$-homocysteine-,
(amino acid)$^1$-(amino acid)$^2$-penicillamine-,
(amino acid)$^1$-(amino acid)$^2$-2-mercaptoethylamine-,
(amino acid)$^1$-(amino acid)$^2$-2-mercaptopropylamine-,
(amino acid)$^1$-(amino acid)$^2$-2-mercapto-2-methylpropylamine-,
(amino acid)$^1$-(amino acid)$^2$-3-mercaptopropylamine-,
wherein (amino acid) in a primary α- or β-amino acid not comprising a thiol group and wherein the chelator is attached to either a targeting moiety or a linker group via a covalent bond with the carboxyl terminus of the chelator or a side chain on one of the amino acid groups.

Most preferred chelators also include chelators of the above formula wherein (amino acid)$^1$ is either an α,ω- or β,ω-amino acid wherein the α- or β-amino group is a free amine and the α,ω- or β,ω-amino acid is covalently linked via the ω amino group.

Other most preferred chelators include those selected from the group consisting of:
-cysteine-(amino acid)-(α,β- or β,γ-diamino acid);
-isocysteine-(amino acid)-(α,β- or β,γ-diamino acid);
-homocysteine-(amino acid)-(α,β- or β,γ-diamino acid);
-penicillamine-(amino acid)-(α,β- or β,γ-diamino acid);
2-mercaptoacetic acid-(amino acid)-(α,β- or β,γ-γ-diamino acid);
2- or 3-mercaptopropionic acid-(amino acid)-(α,β- or β,γ-diamino acid);
2-mercapto-2-methylpropionic acid-(amino acid)-(α,β- or β,γ-diamino acid);
wherein (amino acid) in a primary α- or β-amino acid not comprising a thiol group and wherein the chelator is attached to either a targeting moiety or a linker group via a covalent bond with the amino terminus of the chelator or a side chain on one of the amino acid groups.

Particularly preferred metal chelators are selected from the group consisting of: Gly-Gly-Cys-, Arg-Gly-Cys-, -(ε-Lys)-Gly-Cys-, -(δ-Orn)-Gly-Cys-, -(-γ-Dab)-Gly-Cys-, and -(β-Dap)-Gly-Cys-. (In these formulae, it will be understood that: ε-Lys represents a lysine residue in which the ε-amino group, rather than the typical α-amino group, is covalently linked to the carboxyl group of the adjacent amino acid to form a peptide bond; δ-Orn represents an ornithine residue in which the δ-amino group, rather than the typical α-amino group, is covalently linked to the carboxyl group of the adjacent amino acid to form a peptide bond; γ-Dab represents a 2,4-diaminobutyric acid residue in which the γ-amino group is covalently linked to the carboxyl group of the adjacent amino acid to form a peptide bond; and β-Dap represents a 1,3-diaminopropionic acid residue in which the β-amino group is covalently linked to the carboxyl group of the adjacent amino acid to form a peptide bond.)

An example of preferred chelating moieties of structure type (III) above is the chelator Gly-Gly-Cys- which forms a chelating moiety having the structure:

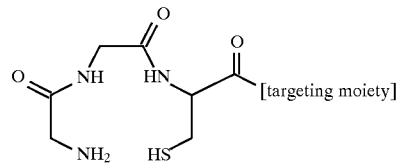

VII.

Chelating ligands having structure type VII form oxotechnetium complexes having the structure:

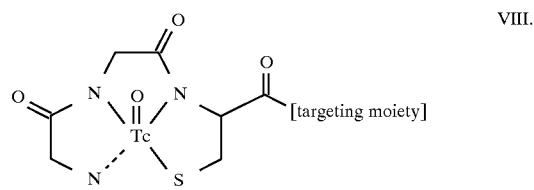

VIII.

An example of more preferred chelating moieties having structure type V as shown above is Lys-(ω-peptide)-Gly-Cys.amide which forms a chelating moiety of structure:

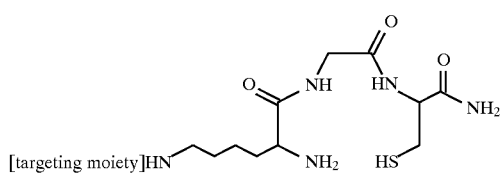

Chelating ligands having structure type IX form oxotechnetium complexes having the structure:

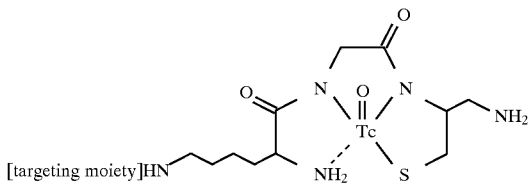

An example of a reagent for preparing a radiopharmaceutical agent as provided by this invention comprising a chelating moiety having structure type II as shown above is (targeting moiety)-Cys-Gly-α,β-diaminopropionamide which forms a chelating moiety of structure:

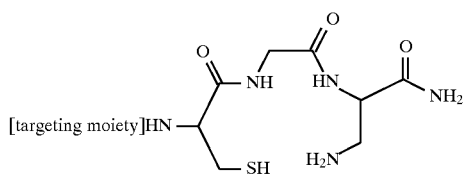

Radiodiagnostic agents having structure type XI form oxotechnetium complexes having the structure:

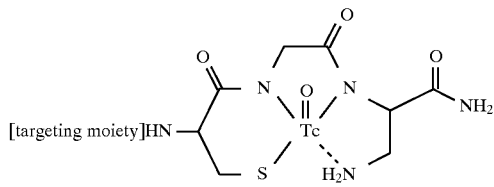

This invention also provides methods for preparing peptide reagents of the invention by chemical synthesis in vitro. In a preferred embodiment, receptor binding VIP peptides are synthesized by solid phase peptide synthesis.

This invention provides reagents for preparing a radiolabeled VIP receptor-binding agent comprising the VIP receptor-binding receptor binding VIP peptides of the invention covalently linked to a chelating moiety. In a preferred embodiment, the reagent is radioactively labeled with Tc-99m. In another preferred embodiment, the reagent is radioactively labeled with $^{186}$Re or $^{188}$Re.

The invention also comprises agents that are complexes of the VIP receptor-binding peptide reagents of the invention with a radioisotope, as well as methods for radiolabeling the peptide reagents of the invention. For example, scintigraphic imaging agents provided by the invention comprise Tc-99m labeled complexes formed by reacting the peptide reagents of the invention with Tc-99m in the presence of a reducing agent. Preferred reducing agents include but are not limited to dithionite ion, stannous ion and ferrous ion. Such Tc-99m complexes of the invention are also formed by labeling the peptide reagents of the invention with Tc-99m by ligand exchange of a prereduced Tc-99m complex as provided herein.

The invention also provides kits for preparing radiolabeled VIP- analogue, receptor binding VIP peptides from the peptide reagents of the invention. Kits for radiolabeling the peptide reagents of the invention are comprised of a sealed vial containing a predetermined quantity of a peptide reagent of the invention and a sufficient amount of reducing agent to radiolabel the reagent. In one aspect of preferred embodiments of the kits of the invention are kits for radiolabeling the peptide reagents of the invention with Tc-99m. Kits for preparing radiotherapeutic agents are also provided, wherein the preferred radioisotopes are rhenium-186 and rhenium-188.

This invention provides methods for using the radiolabeled VIP receptor-binding peptide reagents of the invention diagnostically and therapeutically. In one embodiment of the invention, methods are provided for using scintigraphic imaging agents that are Tc-99m labeled peptide reagents for imaging sites within a mammalian body by obtaining in vivo gamma scintigraphic images. These methods comprise administering an effective diagnostic amount of radiolabeled peptide reagents of the invention and detecting the gamma radiation emitted by the radiolabel localized at the site within the mammalian body.

The invention also provides methods for alleviating VIP-related diseases in animals, preferably humans, comprising administering a therapeutically effective amount of the radiolabeled VIP-binding peptide reagents of the invention to the animal. In preferred embodiments, the reagent is radioactively labeled with $^{186}$Re or $^{188}$Re.

This invention also provides VIP receptor-binding peptides covalently linked to a metal-binding moiety that are complexed with a magnetic, paramagnetic, supermagnetic, or superparamagnetic metal atom, ion or particle, and methods for using such complexes for magnetic-based detection of localization of such receptor binding VIP peptide complexes at tumor or other tissue sites in vivo. Thus, the invention provides non-radioactive methods for localizing tumor and other VIP receptor expressing tissues in vivo.

The receptor binding VIP peptides and receptor binding VIP peptide reagents of the invention may also be comprised of a polyvalent linking moiety. Polyvalent linking moieties of the invention are comprised of at least 2 identical linker functional groups capable of covalently bonding to VIP analogue receptor binding VIP peptides or chelating moieties or both. Preferred linker functional groups are primary or secondary amines, hydroxyl groups, carboxylic acid groups or thiol-reactive groups. In preferred embodiments, the polyvalent linking moieties are comprised of bis-succinimidylmethylether (BSME), 4-(2,2-dimethylacetyl) benzoic acid (DMBA), N-{2-(N',N'-bis(2-succinimidoethyl)aminoethyl)}-N$^6$,N$^9$-bis (2-methyl-2-mercaptopropyl)-6,9-diazanonanamide (BAT-BS), ttis (succinimidylethyl)amine (TSEA), bis-succinimidohexane (BSH), 4-(O—CH$_2$CO-Gly-Gly-Cys. amide)-2-methylpropiophenone (ETAC), tris(acetamidoethyl)amine, bis-acetamidomethyl ether, bis-acetamidoethyl ether, α,ε-bis-acetyllysine, lysine and 1,8-bis-acetamido-3,6-dioxaoctane, or derivatives thereof.

Specific preferred embodiments of the present invention will become evident from the following more detailed description of certain preferred embodiments and the claims.

DETAILED DESCRIPTION OF THE INVENTION

The present invention provides receptor binding VIP peptides and derivatives and analogues thereof that are useful as reagents in the preparation of receptor binding VIP radiopharmaceutical agents for diagnosis and therapy.

Embodiments of these receptor binding VIP peptides provided by this invention are receptor binding VIP peptide reagents wherein the receptor binding VIP peptides, derivatives and analogues thereof are covalently linked to a chelating moiety. Such receptor binding VIP peptide reagents are capable of being radiolabeled to provide radiodiagnostic or radiotherapeutic agents. One example of a radiodiagnostic application using the radiolabeled agents of the invention is scintigraphic imaging, wherein the location and extent of VIP receptor-bearing tumors may be determined. The receptor binding VIP peptide reagents of the invention can also advantageously be radiolabeled with cytotoxic radioisotopes such as rhenium-186 or rhenium-188 for radiotherapeutic uses.

The term scintigraphic imaging agent as used herein is meant to encompass a radiolabeled agent capable of being detected with a radioactivity detecting means (including but not limited to a gamma-camera or a scintillation detector probe).

Radiotherapeutic embodiments of the invention, on the other hand, are advantageously labeled with rhenium-186 and rhenium-188. Such embodiments are useful in the treatment of VIP-related diseases or other ailments in animals, preferably humans, including but not limited to colorectal cancer and other diseases characterized by the growth of malignant or benign tumors capable of binding VIP or VIP analogues via the expression of VIP receptors on the cell surface of cells comprising such tumors.

For the purposes of this invention, the term "VIP receptor binding affinity" is intended to mean binding affinity as measured by any methods known to those of skill in the art, including, inter alia, those methods which measure binding affinity by a dissociation constant, an inhibition constant or an $IC_{50}$ value. The term "having an affinity of at least one-tenth the affinity of radioiodinated VIP" is intended to mean that the affinity is not less than ten times less than the affinity of radioiodinated VIP, or that the inhibition constant ($K_i$) or $IC_{50}$ is not more than 10 times that of radioiodinated VIP.

In the chelating moieties and receptor binding VIP peptides covalently linked to such moieties that contain a thiol covalently linked to a thiol protecting group {(pgp)$^S$} provided by the invention, the thiol-protecting groups may be the same or different and may be but are not limited to:

—CH$_2$-aryl (aryl is phenyl or alkyl or alkyloxy substituted phenyl);
—CH-(aryl)$_2$, (aryl is phenyl or alkyl or alkyloxy substituted phenyl);
—C-(aryl)$_3$, (aryl is phenyl or alkyl or alkyloxy substituted phenyl);
—CH$_2$-(4-methoxyphenyl);
—CH-(4-pyridyl)(Phenyl)$_2$;
—C(CH$_3$)$_3$
-9-phenylfluorenyl;
—CH$_2$NHCOR (R is unsubstituted or substituted alkyl or aryl);
—CH$_2$-NHCOOR (R is unsubstituted or substituted alkyl or aryl);
—CONHR (R is unsubstituted or substituted alkyl or aryl);
—CH$_2$—S—CH$_2$-phenyl Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

For the purposes of this invention, the term "receptor binding vasoactive intestinal peptide (VIP)" is intended to encompass naturally-occurring VIP, fragments, analogues and derivatives thereof that specifically bind to the VIP receptor expressed in a variety of cell types recognized by those with skill in the art. Compounds designed to mimic the receptor-binding properties of VIP are also included in this definition and encompassed by the invention.

Particularly preferred embodiments of the reagents of the invention include:

HSDAVFTDNYTRLRKQMAVKKYLNSILN(ε-K)GC.amide
HSDAVFTDNYTRLRKQMAVKKYLNSIL-NGGC.amide (SEQ. ID NO.2)
AGCHSDAVFTDNYTRLRKQMAVKKYLN-SILN.amide (SEQ. ID NO.3)
and
HSDAVFTDNYTRLRKQMAVKKYLNSILNC(BAT).amide. (SEQ. ID NO.4)

All naturally-occurring amino acids are abbreviated using standard abbreviations (which can be found in G. Zubay, *Biochemistry* (2d. ed.), 1988 (MacMillen Publishing: New York) p.33). For the purposes of this invention, the naturally-occurring amino acids are characterized as lipophilic (alanine, isoleucine, leucine, methionine, phenylalanine, tyrosine, proline, tryptophan and valine, as well as S-alkylated derivatives of cysteine), hydrophilic (asparagine, glutamine, threonine, serine), acidic (glutamic acid and aspartic acid), basic (arginine, histidine and lysine). ε-K is intended to represent a covalent linkage via the ε-amino group on the sidechain of a lysine residue. δ-Orn represents an ornithine residue in which the δ-amino group, rather than the typical α-amino group, is covalently linked to the carboxyl group of the adjacent amino acid to form a peptide bond. γ-Dab represents a 2,4-diaminobutyric acid residue in which the γ-amino group is covalently linked to the carboxyl group of the adjacent amino acid to form a peptide bond. β-Dap represents a 1,3-diaminopropionic acid residue in which the β-amino group is covalently linked to the carboxyl group of the adjacent amino acid to form a peptide bond. (BAT) represents $N^6,N^9$-bis (2-mercapto-2-methyl-propyl)-6,9-diazanonanoic acid; K.(BAT) and Lys.(BAT) represent the amino acid lysine, acylated at the ε-amino group on the amino acid sidechain to (BAT); C(BAT) and Cys(BAT) represent S-($N^6,N^9$-bis(2-mercapto-2methylpropyl)-6,9--diazanonan-l-yl)cysteine; (BAM) is ($N^1,N^4$-bis(2-mercapto-2-methylpropyl)-1,4,10-triazadecane; (BAT-BM) is N-{2-(N',N'-bis(2-maleimidoethyl)aminoethyl}-$N^9$-(t-butoxycarbonyl)-$N^6$, $N^9$-bis (2-methyl-2-triphenyl-methylthiopropyl)-6,9-diazanonanamide; (BAT-BS) is N-{2-(N',N'-bis(2-succinimidoethyl) aminoethyl)-$N^6$, $N^9$-bis(2-mercapto-2-methylpropyl)-6, 9-diazanonanamide; (BMME) is bis-maleimidomethylether; and (BSME) is bis-succinimidomethylether. As used herein, the following amino acids and amino acid analogues are intended to be represented by the following abbreviations: Acm is the sulfhydryl protecting group acetamidomethyl; Pen is penicillamine; Aca is 6-aminocaproic acid; Hly is homolysine; Apc is; $F_D$ is D-phenylalanine; $W_D$ is D-tryptophan; $Y_D$ is D-tyrosine; Cpa is L-($^4$-chlorophenyl)alanine; Thp is 4-amino-tetrahydrothiopyran-4-carboxylic acid; Dpg is dipropylglycine; Nle is norleucine; Hcy is homocysteine; Hhc is homohomocysteine; Aib is aminoisobutyric acid; Nal is 2-naphthylalanine; D-Nal is D-$^2$-naphthylalanine; Ain is 2-aminoindan-2-carboxylic acid; Achxa is 4-amino-cyclohexylalanine; Amf is 4-aminomethyl-phenylalanine;

Aec is S-(2-aminoethyl)cysteine; Aes is O-(2-aminoethyl) serine; Aps is O-(3-aminopropyl)serine; Abu is 2-aminobutyric acid; and Nva is norvaline.

Receptor binding VIP peptides and derivatives and analogues thereof provided by the present invention can be chemically synthesized in vitro. Peptides of the present invention can generally advantageously be prepared on a peptide synthesizer. The peptides of this invention are synthesized wherein the chelating moiety is covalently linked to the peptide during chemical synthesis in vitro, using techniques well known to those with skill in the art. Such peptides covalently-linked to the chelating moiety during synthesis are advantageous because specific sites of covalent linkage can be determined.

Chelating moieties of the invention are introduced into the target receptor binding VIP peptide, derivative or analog during peptide synthesis. This invention provides for the incorporation of chelating moieties in a site-selective fashion into virtually any position in the peptide. The invention in particular provides amino acid derivatives comprising radiolabel chelating moieties linked to an amino acid sidechain, wherein the chelator is incorporated into the peptide during in vitro peptide synthesis at a specific position in the peptide. The invention also provides peptides wherein the radiolabel chelating moieties are incorporated into the peptide at the carboxyl terminus. In preferred embodiments, the radiolabel chelating moiety is incorporated into a sidechain of an amino acid of the peptide, wherein the amino acid is an amino acid in the sequence -SDAVFTDNYTRLRKQMAVKKYLNSILN.amide (SEQ. ID NO.5)

of the peptide. In other preferred embodiments, the radiolabel chelating moiety is incorporated into the synthetic, vasoactive intestinal peptide at a site that is in the sidechain of an amino acid of the peptide, wherein the amino acid is an amino acid in the sequence -NYTRLRKQMAVKKYLNSILN.amide (SEQ. ID NO.6)

of the peptide. In other preferred embodiments, the radiolabel chelating moiety is incorporated into the synthetic, vasoactive intestinal peptide at a site that is in the sidechain of an amino acid of the peptide, wherein the amino acid is an amino acid in the sequence -KQMAVKKYLNSILN.amide (SEQ. ID NO.7)

of the peptide.

In yet further preferred embodiments, the radiolabel chelating moiety is incorporated into the synthetic, vasoactive intestinal peptide at the carboxyl terminus of the peptide.

It is a particular advantage of the reagents of the invention that they are provided having the radiolabel chelating moiety incorporated into the peptide during synthesis. This is advantageous because it allows placement of the chelator at a known position in VIP, or in the VIP fragment, analogue or derivative so as to avoid decreasing the affinity of the peptide for the VIP receptor. Methods for introducing chelators into peptides known in the prior art have been developed predominantly from methods first developed for protein, which, being much larger than peptides, are not as sensitive to the effects of non-site-specific introduction of the chelating moiety. Peptides produced using prior art methods are disadvantageous as compared with the site-specific introduction of the chelators in the peptides of this invention due to the likelihood of introducing the chelator in such a way as to decrease peptide binding affinity, when using the methods of the prior art.

It is also an advantage of this invention that the peptides are provided as chemically-synthesized peptides. This is because chemical synthesis is a controlled process amenable to chemical engineering techniques that are capable of providing a quality-controlled and pharmaceutically-suitable product. Chemical synthesis methods are preferred over other methods, such as biological synthesis and extraction, which may involve the introduction of pathogens (viruses, mycoplasma, etc.) which require costly expenditures to remove or prove absent. Products prepared by chemical synthesis are less expensive to produce and more amenable to successful regulatory approval, thereby impacting the ability to expeditiously bring pharmaceutical embodiments into the clinic and to market.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium- or rhenium-labeled peptides is provided. An appropriate amount of the peptide reagent is introduced into a vial containing a reducing agent, such as stannous chloride, in an amount sufficient to label the peptide with Tc-99m, Re-186 or Re-188. An appropriate amount of a transfer ligand as described (such as tartrate, citrate, gluconate, glucoheptanate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Tc-99m, Re-186 and Re-188 labeled radiopharmaceuticals according to the present invention may be prepared by the addition of an appropriate amount of Tc-99m, Re-186 or Re-188, or radionuclide complexes thereof, into the vials and reaction under conditions described in Example 2 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The imaging reagents provided by the present invention can be used for visualizing sites of expression or hyperexpression of VIP receptors, including organs such as the colon for diagnosing disorders in these organs, and tumors, in particular gastrointestinal tumors, specifically colorectal tumors that can be imaged. In accordance with this invention, the Tc-99m labeled peptide reagents are administered in a single unit injectable dose. The Tc-99m labeled peptide reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

This invention also provides peptides radiolabeled with cytotoxic radioisotopes such as rhenium-186 or rhenium-188 that may be used for radiotherapy of certain tumors as described above. For this purpose, an amount of radioactive isotope from about 10 mCi to about 200 mCi may be administered via any suitable clinical route, preferably by intravenous injection.

This invention also provides VIP receptor-binding peptides covalently linked to a metal-binding moiety that are complexed with a magnetic, paramagnetic, supermagnetic, or superparamagnetic metal atom, ion or particle, and methods for using such complexes for magnetic-based detection of localization of such receptor binding VIP peptide complexes at tumor or other tissue sites in vivo. Thus, the invention provides non-radioactive methods for localizing tumor and other VIP receptor expressing tissues in vivo.

This invention provides methods for using the diagnostic and radiodiagnostic and therapeutic and radiotherapeutic agents of the invention. For radiolabeled embodiments of the agents of the invention, for example, Tc-99m labeled scintigraphic imaging agents, an effective diagnostic or therapeutic amount of the diagnostic or radiodiagnostic or therapeutic or radiotherapeutic agent of the invention are administered. In radiodiagnostic embodiments, localization of the radiolabel is detected using conventional methodologies such as gamma scintigraphy. In non-radioactive diagnostic embodiments, localization of sites of accumulation of the paramagnetic metal-labeled diagnostic agents of the invention is achieved using magnetic resonance imaging methodologies. For the purposes of this invention, radiotherapy is defined as a therapeutic effect ranging from pain palliation to cure.

The imaging agents provided by the invention have utility for tumor imaging, particularly for imaging primary and metastatic neoplastic sites wherein said neoplastic cells express VIP receptors, and in particular such primary and especially metastatic colorectal tumor cells that have been clinically recalcitrant to detection using conventional methodologies.

Those having skill in this art will recognize that efficacious radiopharmaceuticals can be identified, tested and characterized using any of a number of in vitro methodologies known in the art. Such methodologies include, inter alia, the determination of dissociation constants or inhibition constants of binding of the radiopharmaceuticals of the invention to their cognate VIP receptors, as well as comparison of the affinity or avidity of such binding with binding of radiolabeled, for example, $^{125}$I-labeled, VIP itself, and in experiments wherein a radiopharmaceutical of the invention is used in competition with radiolabeled VIP, or in the converse experiments using unlabeled VIP in competition with radiopharmaceutical of the invention.

In the practice of this invention, effective radiodiagnostic and radiotherapeutic agents are prepared as follows. Reagents of the invention comprising receptor binding VIP, and VIP fragments, analogues and derivatives thereof, are synthesized using the methods of the invention wherein the chelating moiety is incorporated into the peptide during synthesis. The reagents of the invention are then complexed with rhenium, preferably as ReO, as further disclosed herein. VIP receptor binding is then evaluated in in vitro competition binding assays as described herein using radioiodinated VIP, as disclosed in Example 4 below.

The methods for making and labeling these compounds are more fully illustrated in the following Examples. These Examples illustrate certain aspects of the above-described method and advantageous results, and are shown by way of illustration and not limitation.

EXAMPLE 1

Synthesis of BAT Chelators

A. Synthesis of N-Boc-N'-(5-carboxypentyl)-N,N'-bis (2-methyl-2-triphenylmethylthiopropyl)ethylenediamine a. 2-methyl-2-(triphenlmethylthio)propanal Triphenylmethylmercaptan (362.94 g, 1.31 mol, 100 mol %) dissolved in anhydrous THF (tetrahydrafuran; 2 L) was cooled in an ice bath under argon. Sodium hydride (60% in oil; 54.39 g, 1.35 mol, 104 mol %) was added in portions over 20 min. 2-bromo-2-methylpropanal (206.06 g, 1.36 mol, 104 mol %; see Stevens & Gillis, 1957, *J. Amer. Chem. Soc.* 79: 3448–51) was then added slowly over 20 min. The reaction mixture was allowed to warm to room temperature and stirred for 12 hours. The reaction was quenched with water (1 L) and extracted with diethyl ether (3×1 L). The ether extracts were combined, washed with saturated NaCl solution (500 mL), dried over $Na_2SO_4$ and filtered. The solvent was removed under reduced pressure to afford a thick orange oil. The crude oil was dissolved in toluene (200 mL) and diluted to 2 L with hot hexanes. The mixture was filtered through a sintered glass funnel and cooled at −5° C. for 12 hours. The white crystalline solid which formed was removed by filtration to afford 266.36 g (59% yield) of the title compound. The melting point of the resulting compound was determined to be 83°–85° C. Nuclear magnetic resonance characterization experiments yielded the following molecular signature:

$^1$H NMR(300 $MH_z$, $CDCl_3$): δ1.24(s, 6H, $2CH_3$), 7.2–7.35 (m, 9H), 7.59–7.62 (m,6H), 8.69 (s, H, —COH)

$^{13}$C NMR (75 $MH_z$, $CDCl_3$): δ6 22.86, 55.66, 67.48, 126.85, 127.75, 129.72, 144.79, 197.31.

b. N.N'-bis(2-methyl-2-triphenylmethylthiopropyl) ethylenediamine.

Ethylenediamine (1.3 mL, 0.0194 mol, 100 mol %) was added to 2-methyl-2-(triphenylmethylthio)propanal (13.86 g, 0.0401 mol, 206 mol %) dissolved in methanol (40 mL) and anhydrous THF (40 mL) under argon, and the pH was adjusted to pH 6 by dropwise addition of acetic acid. The solution was stirred for 20 min at 20° C. Sodium cyanoborohydride (1.22 g, 0.0194 mol, 100 mol %) was added and the reaction was stirred at room temperature for 3 hours. Additional sodium cyanoborohydride (1.08 g) was added and the reaction was stirred at 20° C for 17 hours. A final portion of sodium cyanoborohydride (1.02 g) was added and the reaction heated at reflux under argon for 6 hours. The reaction was quenched with 0.5M HC1 (100 mL) and extracted with ethyl acetate (2×100 niL). The organic extracts were combined, sequentially washed with 2M NaOH (60 mL), saturated NaCl solution (60 mL), dried (Na$_2$SO$_4$), and filtered. The solvent was removed under reduced pressure to give 16.67 g of crude product which was crystallized from toluene/hexanes to afford 10.20 g (73% yield) of white crystals of the title compound. The melting point of the resulting compound was determined to be 83°–86° C. FABMS analysis yielded an m/z of 721 (MH+). Nuclear magnetic resonance characterization experiments yielded the following molecular signature:

$^1$H NMR (300 MH$_z$, CDCl$_3$): δ 1.12 (s, 12H, 4 CH$_3$), 1.64 (s, 4H, N—CH$_2$—C(Me)$_2$—S), 2.52 (s, 4H, N—CH$_2$—CH$_2$—N), 5.31 (S, 2H, 2—NH), 7.12–7.30 (m, 18H, Ar), 7.62–7.65 (m, 12H, Ar).

c. N-(5-carboxypentyl)-N,N'-bis(2-methyl-2-triphenylmethylthiopropyl)ethylenediamine K$_2$CO$_3$ (1.92 g, 13.9 mmol, 100 mol %) was added to N,N'-bis (2-methyl-2-triphenylmethylthiopropyl) ethylenediamine (10.03 g, 13.9 mmol) in CH$_3$CN (60 mL), followed by ethyl 5-bromovalerate (3.30 mL, 20.8 mmol, 150 mol %). The reaction was heated at reflux under argon overnight. The solution was then concentrated to a paste and partitioned between 0.25M KOH (100 mL) and ethyl acetate (100 mL). The aqueous layer was extracted with ethyl acetate (1×50 mL) and the combined ethyl acetate layers were washed with 50 mL water and NaCl solution (2×50 mL), dried with Na$_2$SO$_4$ and concentrated to an orange oil. Purification by flash chromatography (300 g flash silica, 100% CHCl$_3$ to 5% MeOH/CHCl$_3$) gave pure title compound (7.75 g, 66% yield). FABMS analysis yielded an (MH+) of 849 (compared with a calculated molecular weight of 849.24 for the compound C$_{55}$H$_{64}$N$_2$O$_2$S$_2$).

d. N-Boc-N'-(5-carboxypentyl)-N,N'-bis (2-methyl-2-triphenylmethylthiopropyl)ethylenediamine 1M KOH (25 mL, 25.0 mmol, 274 mol %) was added to N-(5-carboethoxypentyl)-N,N'-bis (2-methyl-2-triphenylmethylthiopropyl) ethylenediamine (7.75 g, 9.13 mmol) in dioxane (200 mL), followed by water (250 mL). Dioxane was then added dropwise with stirring until a homogeneous solution was obtained. The reaction was heated at a slow reflux overnight. Most of the dioxane was removed by rotary evaporation and the pH of solution was adjusted to ~7–8 with 1M KH$_2$PO$_4$ and saturated NaHCO$_3$. The solution was then extracted with ethyl acetate (3×75 mL) and the combined organic layers were washed with NaCl solution (50 mL), dried with Na$_2$SO$_4$ and concentrated to a foam/solid (6.35 g, 85% yield).

To the crude product from the above reaction was added (BOC)$_2$O (3.35 g, 15.4 immol, 200 mol %), CH$_3$CN (50 mL) and methylene chloride (50 niL), followed by triethylamine (1.0 mL, 7.2 mmol, 93 mol %). The reaction was stirred at room temperature under argon overnight. The reaction solution was then concentrated and partitioned between water (100 mL) and ethyl acetate (50 mL). The aqueous layer was extracted with ethyl acetate (1×50 mL) and the combined ethyl acetate layers were washed with 5% citric acid and NaCl solution (50 mL each), then dried (Na$_2$SO$_4$) and concentrated to an orange oil. Purification by flash chromatography (200 g flash silica, 100% CDCl$_3$ to 5% methanol/chloroform) gave pure title compound (2.58 g, 36% yield). FABMS analysis gave an (MH+) of 921 (compared with the calculated value of 921.31 for the compound C$_{58}$H$_{68}$N$_2$O$_4$S$_2$).

B. Synthesis of N-Boc-N'-(5-carboxypentyl)-N, N'-bis-[2-(4-methoxybenzylthio)-2-methylpropyl]ethylenediamine a. N,N'-bis-[2-(4-methoxybenzylthio)-2-methylpropyl]-ethylenediamine A solution of N,N'-bis(2-mercapto-2-methylpropyl) ethylenediamine (11.23 g, 47.5 mmol; see, DiZio et al., 1991, Bioconjugate Chem 2: 353 and Corbin et al., 1976, J. Org. Chem. 41: 489) in methanol (500 mL) was cooled in ice/water bath and then saturated with gaseous ammonia over 45 min. To this was added 4-methoxybenzyl chloride (17.0 mL, 125 mmol, 264 mol %). The reaction was allowed to warm to room temperature overnight with stirring under argon. The solution was concentrated to a paste and then partitioned between diethyl ether (150 mL) and 0.5M KOH (200 mL). The aqueous layer was further extracted with diethyl ether (2×50 mL). The combined organic layers were washed with NaCl solution and concentrated to a clear colorless oil. The oil dissolved in diethyl ether (200 mL) and then acidified with 4.0M HCl in dioxane until no further precipitation was seen. The white precipitate was collected by filtration and washed with diethyl ether. The white solid was recrystallized from hot water at a pH of ~2. The product was collected by filtration to afford 29.94 g as a mix of mono- and di- HCl salts. The HCl salts were partitioned between 1M KOH (100 mL) and ethyl acetate (100 mL). The aqueous was extracted with ethyl acetate (2×30 mL) and the combined organic layers were washed with NaCl solution, dried with Na$_2$SO$_4$ and concentrated to give pure product as the free base as a light yellow oil (18.53 g, 82% yield). Nuclear magnetic resonance characterization experiments yielded the following molecular signature:

$^1$H NMR (300 MHz, CDCL$_3$): δ 7.25 (d, 4H, J=9), 6.83 (d, 4H, J=9), 3.78 (s, 6H), 3.67 (s, 4H), 2.63 (s, 4H), 2.56 (s, 4H), 1.34 (s, 12H).

b. N-(5-carboethoxypentyl)-N,N'-bis-[2-(4-methoxybenzylthio)-2-methylpropyl]ethylenediamine To N,N'-bis-[2-(4-methoxybenzylthio)-2-methylpropyl]-ethylenediamine (4.13 g, 8.66 mmol) in CH$_3$CN (50 mL) was added K$_2$CO$_3$ (1.21 g, 8.75 mmol, 101 mol %) followed by ethyl 5-bromovalerate (2.80 mL, 17.7 mmol, 204 mol %). The reaction was stirred at reflux overnight and was then concentrated to a paste in vacuo. The residue was partitioned between ethyl acetate (100 mL) and 0.5M KOH (100 mL). The aqueous layer was extracted with ethyl acetate (1×50 mL) and the combined organic layers were washed with NaCl solution (50 mL), dried with Na$_2$SO$_4$ and concentrated to a yellow oil (~6 g). Purification by normal-phase preparative HPLC (100% CHCl$_3$ to 5% methanol/chloroform over 25 min.) afforded pure title compound (1.759 g, 34% yield). FABMS analysis gave an (MH+) of 605 (compared with the value of 604.90 calculated for C$_{33}$H$_{52}$N$_2$O$_4$S$_2$). Nuclear magnetic resonance characterization experiments yielded the following molecular signature:

$^1$H NMR (300 mH$_z$, CDCl$_3$): δ 7.25 (d, 4H, J=8.5), 6.83 (d, 4H, J=8.5), 4.13 (q, 2H J=7), 3.793 (s, 3H), 3.789 (s. 3H), 3.74 (s, 2H), 3.67 (s, 2H), 2.6 (m, 10H), 2.31 (t, 2H, J=7), 1.6 (m, 2H), 1.5 (m 2H), 1.34 (s 12H), 1.28 (t, 3H, J=7).

c. N-Boc-N'-(5-carboxypentyl)-N,N'-bis-[2-(4-methoxybenzylthio)-2-methylpropyl]ethylenediamine To N-(5-carboethoxypentyl)-N,N'-bis-[2-(4-methoxybenzylthio)-2-methylpropyl]ethylenediamine (586 mg, 0.969 mmol) in THF (40 mL) was added water (30 mL) and 1M KOH (2.5 mL, 2.5 mmol, 260 mol %). The homogeneous solution was heated to a slow reflux overnight. The solution was then cooled to room temperature and the THF was removed under rotary evaporation. The residue was diluted to 50 mL with H$_2$O and the pH was adjusted to ~2–3 with 1M HCl. The solution was extracted with ethyl acetate (3×30 mL) and the combined organic layers were washed with NaCl solution (50 mL), dried with Na$_2$SO$_4$ and concentrated to give crude acid (422 mg, 75% yield).

To the crude product from the above reaction was added CH$_3$CN (40 mL) and (BOC)$_2$O (240 mg, 1.10 mmol, 150 mol %) followed by triethylamine (0.200 mL, 1.43 mmol, 196 mol %). The homogenous solution stirred at room temperature overnight under argon. The solution was then concentrated to a paste and partitioned between ethyl acetate (25 mL) and 1M $KH_2PO_4$ (25 mL). The organic layer was washed with 5% citric acid (2×25 mL) and NaCl solution (25 mL), dried with $Na_2SO_4$ and concentrated to a yellow oil. Purification by flash chromatography (50 mL flash silica gel, 100% chloroform to 15% methanol/ chloroform) gave pure title compound (344 mg, 70% yield). FABMS analysis gave an (MH+) of 677 (compared to the value of 676.97 calculated for the compound $C_{36}H_{56}N_2O_6S_2$). Nuclear magnetic resonance characterization experiments yielded the following molecular signature:

$^1$H NMR (300 MHz, $CDCl_3$): δ 7.20 (d, 4H, J=7), 6.79 (d, 4H, J=7), 3.75 (S, 3H), 3.74 (S, 3H), 3.68 (M, 4H), 3.35 (M, 4H), 2.65 (M, 2H), 2.53 (M, 4H), 2.31 (M, 2H), 1.59 (M, 2H), 1.43 (S, 11H), 1.30 (S, 6H), 1.26 (S, 6H)

C. Synthesis of BAT-BM (N-[2-(N',N'-bis(2-maleimidoethyl)aminoethyl)]-$N^6$, $N^9$-bis (2-methyl-2-triphenylmethylthiopropyl)-6,9-diazanonanamide)

BAT-BM was prepared as follows. BAT acid ($N^9$-(t-butoxycarbonyl)-$N^6$,$N^9$-bis (2-methyl-2-triphenylmethylthiopropyl)-6,9-diazanonanoic acid) (10.03 g, 10.89 mmol) and 75 mL of dry methylene chloride ($CH_2Cl_2$) were added to a 250 mL round-bottomed flask equipped with magnetic stir bar and argon balloon. To this solution was added diisopropylcarbodiimide (3.40 mL, 21.7 mmol, 199mole %), followed by N-hydroxy-succinimide (3.12 g, 27.1 mmol, 249 mole %). This solution was observed to become cloudy within 1 h, and was further incubated with stirring for a total of 4 h at room temperature. A solution of tris(2-aminoethyl)amine (30 mL, 200 mmol, 1840 mole %) in 30 mL methylene chloride was then added and stirring continued overnight. The reaction mixture was then concentrated under reduced pressure, and the residue partitioned between ethylacetate (150 mL) and 0.5M potassium carbonate ($K_2CO_3$; 150 mL). The organic layer was separated, washed with brine and concentrated to give the crude product N-[2-(N',N'-bis (2-aminoethyl)aminoethyl)]-$N^9$-(t-butoxycarbonyl)-$N^6$,$N^9$-bis (2-methyl-2-triphenylmethylthiopropyl)-6,9-diazanonanamide as a foam/oil.

This crude product was added to a 1000 mL round-bottomed flask, equipped with magnetic stir bar, containing 300 mL THF, and then 30 mL saturated sodium bicarbonate ($NaHCO_3$), 100 mL water and N-methoxycarbonyhnaleimide (6.13 g, 39.5 mmol, 363 mole %) were added. This heterogeneous mixture was stirred overnight at room temperature. THF was removed from the mixture by rotary evaporation, and the aqueous residue was twice extracted with ethylacetate (2×75 mL). The combined organic layers of these extractions were washed with brine, dried over sodium sulfate, filtered through a medium frit and concentrated to about 12 g of crude product. Purification by liquid chromatography (250 g silicon dioxide/ eluted with a gradient of chloroform→2% methanol in chloroform) afforded 5.3 g of pure product (N-[2-(N',N'-bis(2-maleimidoethyl)aminoethyl)]-$N^9$-(t-butoxycarbonyl)-$N^6$, $N^9$-bis(2-methyl-2-triphenylmethylthiopropyl)-6,9-diazanonanamide) (equivalent to 40% yield), along with approximately 5 g of crude product that can be re-purified to yield pure product. Chemical analysis of the purified product confirmed its identity as BAT-BM as follows:

$^1$H NMR (200 mHz, $CDCl_3$): δ 0.91 (12H,s), 1.38 (9H,s), 1.2–1.6 (4H,m), 2.06 (2H,s), 2.18 (2H,t,J=7), 2.31 (4H,m), 2.55 (2H,t,J=5), 2.61 (4H,t,J=6), 2.99 (2H,s), 3.0–3.3 (4H, m), 3.46 (4H,t,J=6), 6.49 (—NH,t,J=4), 6.64 (4H,s), 7.1–7.3 (18H,m), 7.6 (12H,t,J=17)

D. Synthesis of [BAT]-conjugated(εN) Lys(αN-Fmoc) [N-ε-($N^9$-t-butoxycarbonyl)-$N^6$,$N^9$-bis [2-methyl-2-(triphenylmethylthio)propyl]-6,9-diazanonanoyl)-N-α-Fmoc-lysine A 100 mL single-necked round-bottomed flask, equipped with stir bar and argon balloon, was charged with $N^9$-(t-butoxycarbonyl)-$N^6$,$N^9$-bis[2-methyl-2-(triphenylmethylthio) propyl]-6,9-diazanonanoic acid (BAT acid; 3.29 g, 3.57 mmol) in 50 mL $CH_2Cl_2$ at room temperature. To this was added diisopropylcarbodiimide (DIC; 580 μL, 3.70 mmol, 104 mole %) followed immediately by N-hydroxysuccinimide (HOSu; 432mg, 3,75 mmol, 105 mole %). The reaction was stirred overnight at room temperature during which time a white precipitate developed. The mixture was filtered and the filtrate concentrated to a solid foam. The crude foam, in a 100 mL round-bottomed flask, was dissolved in 75 mL of a 2:1 mixture of dimethoxyethane and water. To this homogeneous solution was added N-α-Fmoc-lysine hydrochloride (1.52 g, 3,75 mmol, 105 mole %) followed by $K_2CO_3$ (517 mg, 3,74 mmol, 105 mole %), and the yellow solution stirred overnight at room temperature. The solution was then poured into a 250 mL erlenmeyer flask containing 100 mL of ethyl acetate and 100 mL of water. The organic layer was separated and the aqueous layer further extracted with 50 mL ethyl acetate. The combined organic layers were washed once with brine (100 mL), dried over $Na_2SO_4$ and concentrated to a yellow solid. This crude product was purified by low-pressure liquid chromatography (150 g $SiO_2$, eluted with $CHCl_3$→10% methanol in $CHCL_3$). In this way, 3.12 g of the named compound was prepared (69% yield). Chemical analysis of the purified product confirmed its identity as follows:

$^1$H NMR (300 MHz, $CDCl_3$): δ 0.88 (12H,s,broad), 1.05–1.45 (19H,m), 1.8–2.1 (4H,m), 1.8–2.47 (4H,m), 2.75–3.2 (6H,m), 3.9–4.3 (4H,m,), 7.2 (22H,m), 7.6 (16H, s,bound). FABMS $MH^+$ was predicted to be 1270.6 and found to be 1272.

E. Synthesis of BAM ($N^1$-(t-butoxycarbonyl)-$N^1$,$N^4$-bis [2-methyl-2-(triphenylmethylthio)propyl]-1,4,10-triazadecane A 250 mL single-necked round-bottomed flask, equipped with a stir bar, reflux condenser and argon balloon, was charged with $N^1$,$N^4$-bis[2-methyl-2-(triphenylmethylthio) propyl]-ethylenediamine (BAT-I; 10.0 g, 14.01 mmol) in 50 mL of $CH_3CN$ and 30 mL dioxane. To this was added N-(5-bromopentyl)-phthalimide (8.04 g, 27.1 mmol, 194 mole %) followed by $K_2CO_3$ (2.95 g, 21.3 mmol, 152 mole %). The mixture was heated at reflux under argon for two days. The reaction mixture was then concentrated and the residue partitioned between 150 mL water and 150 mL ethyl acetate. The organic layer was separated and the aqueous layer (at pH of about 10) was further extracted with 50 mL ethyl acetate. The combined organic layers were washed once with brine (75 mL), dried over $Na_2CO_3$ and concentrated to an oil. Purification by low-pressure liquid chromatography (300 g $SiO_2$, $CHCl_3$→2% methanol in $CHCl_3$) afforded 9.20 g of 9-phthalimido-$N^1$, $N^4$-bis[2-methyl-2-(triphenylmethylthio) propyl]-1,4-diazanonane as a yellow foam (70% yield). Chemical analysis of the purified product of this intermediate confirmed its identity as follows:

$^1$H NMR (300 MHz, $CDCl_3$): δ 1.01 (6H,s), 1.03 (6H,s), 1.15–1.4 (2H,t), 1.98 (2H,s), 2.10 (2H,s), 2.28 (2H,m), 2.45 (3H,m), 3.68 (2H,t), 7.15–7.35 (18H, m), 7.62 (12H,t), 7.72 (2H, m), 7.85 (2H,m). FABMS MH+was predicted to be 935.4 and found to be 936.

A 500 mL single-necked round-bottomed flask, equipped with stir bar, was charged with 9-phthalimido-$N^1,N^4$-bis[2-methyl-2-(triphenylmethylthio)propyl]-1,4-diazanonane (8.83 g, 9.43 mmol) in 75 mL of $CH_3CN$ and 20 mL $CH_2Cl_2$. To this was added $K_2CO_3$ (1.30 g, 9,41 mmol, 100 mole %), followed by di-tert-butyl dicarbonate (2.15 g, 9.85 mmol, 104 mole %), and the reaction stirred at room temperature overnight. The reaction mixture was then concentrated and partitioned between 100 mL each of water and ethyl acetate. The organic layer was separated and the aqueous layer was further extracted with 50 mL ethyl acetate. The combined organic layers were washed once with brine (75 mL), dried over $Na_2SO_4$ and concentrated to give 9.69 g of crude 9-phthalimido-$N^1$-(t-butoxycarbonyl)-$N^1$, $N^4$-bis[2-methyl-2-(trphenylmethylthio)propyl ]-1,4-diazanonane as a yellow foam (99% crude yield). This crude product was used without further purification.

A 250 mL single-necked round-bottomed flask, equipped with stir bar and reflux condenser, was charged with 9-phthalimido-$N^1$-(t-butoxycarbonyl)-$N^1$, $N^4$-bis[2-methyl-2-(triphenylmethylthio)propyl ]-1,4-diazanonane (5.50 g, 5.319.43 mmol) in 25 mL of THF. To this was added 100 mL ethanol and 5 mL water. The addition of water caused the starting material to precipitate out of solution. Hydrazine hydrate (1.2 mL, 24.7 mmol, 466 mole %) was added, and the reaction heated at reflux for two days. The reaction mixture was concentrated and partitioned between 100 mL each of water and 0.25M $K_2CO_3$. The organic layer was separated and washed once with brine (75 mL), dried over $Na_2SO_4$ and concentrated to a solid foam. Purification of the crude product by low-pressure liquid chromatography (100 g $SiO_2$, $CHCl_3 \rightarrow 5\%$ methanol in $CHCl_3$, the column pretreated with 200 mL 2% triethylamine in $CHCl_3$) afforded 3.27 g of pure $N^1$-(t-butoxycarbonyl)-$N^1,N^4$-bis [2-methyl-2-(triphenylmethylthio)propyl ]-1,4,10-triazadecane as a yellow foam (68% yield). Chemical analysis of the purified product confirmed its identity as follows:

$^1$H NMR (300 MHz, $CDCl_3$): δ 0.9 (12H,s), 1.2 (6H,s), 1.36 (9H,s), 2.05 (4H,m), 2.24 (2H,t), 2.31 (2H,t), 2.62 (3H,t), 3.0 (2H,s,broad), 3.1 (2H,s,broad), 7.2 (18H,m) 7.6 (12H,t). FABMS $MH^+$ was predicted to be 905.5 and found to be 906.5.

F. Synthesis of [BAT]-conjugated(S) Cys(αN-Fmoc)(N (Fmoc)-S-($N^9$-t-butoxycarbonyl)-$N^6$, $N^9$-bis[2-methyl-2-(triphenylmethylthio)propyl]-6,9-diazanonan-1-yl)cysteine)
a. Synthesis of ($N^9$-t-butoxycarbonyl)-$N^6$, $N^9$-bis[2-methyl-2-(triphenylmethylthio)propyl]-6, 9-diazanonan-1-ol (BAT-pentanol)

To a 500 mL round-bottomed flask containing BAT acid (10.4 g, 10.89 mmol) in 250 mL dry THF under argon was added 12.1 mL of 1M $BH_3$-THF (12.1 mmol), the addition being performed slowly over 5 min. Upon addition, foaming occurred. This reaction mixture was incubated with stirring at room temperature overnight. The reaction was quenched with excess methanol (50 mL) and incubated with stirring for an additional 2 h. The solution was concentrated by evaporation and the residue partitioned between 200 mL ethyl acetate, 100 mL 1M citric acid and 100 mL 1M $KH_2PO_4$. The organic layer was isolated and washed sequentially with 100 mL each of water, saturated $NaHCO_3$ and brine. The washed organic layer was then dried over anhydrous $Na_2SO_4$ and concentrated by evaporation to a white foam to give 8.82 g of crude product (89% yield). Chemical analysis of the purified product confirmed its identity as follows:

$^1$H NMR (300 MHz, $CDCL_3$): δ 0.91 (12H,s), 1.2–1.3 (4H,m), 1.38 (9H,s), 1.4–1.6 (4H), 2.08 (1H,s), 2.2–2.4 (4H,m), 2.95–3.05 (2H,br), 3.05–3.25 (2H,br), 3.58 (2H,t, J=6), 7.12–7.28 (18H,m), 7.61 (12H,t,J=7).

b. Synthesis of O-methanesulfonyl-($N^9$-t-butoxycarbonyl)-$N^6,N^9$-bis [2-methyl-2-(triphenlmethylthio)propyl]-6,9-diazanonan-1-ol (BAT-mesylate)

To a 500 mL round-bottomed flask containing BAT-pentanol (8.80 g, 9.70 mmol) in 100 mL dry THF under argon was added 1.6 mL triethylamine (11.5 mmol) followed by 0.83 mL methanesulfonyl chloride (10.7 mmol) with stirring. The solution became cloudy white within a few minutes of these additions. Stirring was continued overnight at room temperature. The solution was concentrated by evaporation and then partitioned between 100 mL ethylacetate and 100 mL 1M $KH_2PO_4$. The ethyl acetate layer was isolated and washed with 100 mL brine, and then dried over anhydrous $Na_2SO_4$ and evaporated to give 9.61 g of crude product (100% yield) as a light yellow foam.

C. Synthesis of S-($N^9$-t-butoxycarbonyl)-$N^6,N^9$-bis[2-methyl-2-(triphenylmethylthio)propyl]-6, 9-diazanonan-1-yl)cysteine (H-Cvs(BAT)-OH)

In a 20 mL scintillation vial was combined cysteine (1.3 g, 10.7 mmol), 4 mL 5.4M sodium methoxide (21.6 mmol) and 5 mL anhydrous methanol. This homogenous solution was added to a solution of BAT-mesylate (9.57 g, 9.71 mmol) in 80 mL anhydrous dimethylformamide (DMF) and stirred overnight at room temperature under argon. The solvents were removed by rotary evaporation under reduced pressure and the residue partitioned between 100 mL ethyl acetate and 100 mL 1M $KH_2PO_4$. The ethyl acetate layer was isolated and washed sequentially with 100 mL each of saturated $NaHCO_3$ and brine, and then dried over anhydrous $Na_2SO_4$ and concentrated by evaporation to yield a white foam. This product was not characterized, but was used immediately in the following synthetic reaction.

d. Synthesis of N-fluorenylmethoxycarbonyl-S-($N^9$-t-butoxycarbonyl)-$N^6,N^9$-bis [2-methyl-2-(triphenylmethythio) propyl]-6,9-diazanonan-1-yl)cysteine (Fmoc-Cys(BAT)-OH)

The crude H-Cys(BAT)-OH prepared as described above was assumed to constitute 9.71 mmol product. The entire amount of this crude product was dissolved in 200 mL THF and 150 mL water in a 1 L Erlenmeyer flask. To this homogeneous solution was added 1.34 g $K_2CO_3$ (9.72 mmol) followed by 3.28 g N-fluorenylmethoxycarbonyloxy-succinimide (9.73 mmol). This reaction mixture was stirred overnight at room temperature. Most of the THF was then removed from the reaction mixture by rotary evaporation, and the remainder partitioned between 100 mL ethylacetate and 100 mL 1M $KH_2PO_4$. The ethylacetate layer was isolated and washed with 50 mL brine, dried over anhydrous $Na_2SO_4$ and concentrated to yield a yellow foam. This crude product was purified by liquid chromatography, using 300 g silica gel and a linear gradient of 0–3% methanol in chloroform. Chromatography yielded 10.1 g pure Fmoc-Cys(BAT)-OH (84% yield from BAT-mesylate). Chemical analysis of the purified product confirmed its identity as follows:

$^1$H NMR (300 MHz, $CDCl_3$): δ 0.85 (12H,s), 1.23 (4H, br), 1.35 (9H,s), 1.5 (2H,m), 2.0–2.15 (2H,m), 2.15–2.35 (4H,m), 2.51 (2H,t,J=6), 2.85–3.05 (4H,m), 3.15 (2H,br), 4.1–4.2 (1H,m), 4.2–4.4 (3H,m), 7.05–7.4 (22H,m), 7.5–7.65 (14H,m), 7.71 (2H,d,J=7)

EXAMPLE 2

Solid Phase Peptide Synthesis

Solid phase peptide synthesis (SPPS) was carried out on a 0.25 millimole (mmole) scale using an Applied Biosystems Model 431 A Peptide Synthesizer and using 9-fluorenylmethyloxycarbonyl (Fmoc) amino-terminus protection, coupling with dicyclohexylcarbodiimide/ hydroxybenzotriazole or 2-(1H-benzotriazol-1-yl)-1,1,3, 3-tetramethyluronium hexafluorophosphate/ hydroxybenzotriazole (HBTU/HOBT), and using p-hydroxymethyl henoxymethyl-polystyrene (HMP) resin or Sasrin™ or chlorotrityl resin for carboxyl-terminus acids or Rink amide resin for carboxyl-terminus amides.

Where appropriate, Fmoc-Cys(BAT) and Nα-Fmoc-Nε-(BAT)Lys were synthesized as described in Example 1.

Where appropriate, 2-chloroacetyl, 2-bromoacetyl and 2-bromo-3-phenylpropionyl groups are introduced either by using the appropriate 2-halo acid as the last residue coupled during SPPS, or by treating the N-terminus free amino acid peptide bound to the resin with either 2-halo acid/ diisopropylcarbodiimide/N-hydroxysuccinimide/NMP or 2-halo acid anhydride/ diisopropylethylamine/NMP.

Where appropriate, HPLC-purified 2-haloacylated peptides are cyclized by stirring an 0.1–1.0 mg/mL solution in phosphate or bicarbonate buffer or dilute ammonium hydroxide (pH 8.0), optionally containing 0.5–1.0 mM EDTA, or acetonitrile or THF for 1–48 h followed optionally by acidification with acetic acid, lyophilization and HPLC purification.

Where appropriate, thiol-containing peptides are reacted with chloroacetyl-containing, thiol-protected Tc-99m complexing moieties at pH 10 for 0.5–4 hours at room temperature, followed by acetic acid acidification and evaporation of the solution to give the corresponding peptide-sulfide adduct. Deprotection and purification are routinely performed as described to yield the chelator-peptide conjugate.

Where appropriate, BSME adducts are prepared by reacting single thiol-containing peptides (5 to 50 mg/mL in DMF buffered to pH 7 with N-methyhnorpholine or N-ethyl-morpholine, or 50 mM sodium phosphate buffer, pH 7–8, optionally containing 0.5 mM EDTA or DMF or THF or acetonitrile) with 0.5 molar equivalents of BMME (bis-maleimidomethylether) pre-dissolved in acetonitrile at room temperature for approximately 1–18 hours. The solution was concentrated and the product was purified by HPLC.

Where appropriate, TSEA adducts are prepared by reacting single thiol-containing peptide (at concentrations of 10 to 100 mg/mL peptide in DMF buffered to pH 7 with N-methylmorpholine or N-ethyimorpholine, or 5 to 50 mg/mL peptide in 50 mM sodium phosphate, pH 7–8, optionally containing 0.5 mM EDTA or DMF or THF or acetonitrile) with 0.33 molar equivalents of TMEA (tris(2-maleimidoethyl)amine) pre-dissolved in acetonitrile or DMF, with or without 1 molar equivalent of triethanolamine, at room temperature for approximately 1–18 h. Such reaction mixtures containing adducts are concentrated and the adducts are then purified using HPLC.

Where appropriate, (BAM) ($N^1,N^4$-bis(2-mercapto-2-methylpropyl)-1,4,10-triazadecane) is conjugated to the peptide by first activating the peptide carboxylate with a mixture of diisopropylcarbodiimide/ N-hydroxysuccinimide or HBTU/HOBt in DMF, NMP or methylene chloride, followed by coupling in the presence of diisopropylethylamine. After coupling, the conjugates are deprotected as described above.

Where appropriate, (BAT) ($N^6,N^9$-bis(2-mercapto-2-methylpropyl)-6,9-diazanonanoic acid) is incorporated into peptides as protected amino acid derivatives, such as (Nα(Fmoc)-Nε(N-Boc)-S, S'-bistrityl-BAT)lysine (prepared from Nα(Fmoc)-lysine and ε(N-Boc)-S, S'-bistrityl-BAT as described in Example 2 of co-owned and co-pending U.S. patent application Ser. No., incorporated by reference), or as (N(Fmoc)-S,S'-bistrityl-BAT)cysteine (prepared as described in Example 1F, above) during peptide synthesis and then deprotected after cleavage of the completed peptide from the synthetic resin.

Where appropriate, BAT-BS (N-{2-(N',N'-bis(2-succinimidoethyl) aminoethyl)}-$N^6,N^9$-bis (2-methyl-2-mercaptopropyl)-6,9-diazanonanamide) adducts are prepared by reacting single thiol-containing peptide (at concentrations of 2 to 50 mg/mL peptide in DMF buffered to pH 7 with N-methylmorpholine or N-ethynorpholine, or in 50 mM sodium phosphate (pH 7–8), optionally containing 0.5 mM EDTA or DMF or THF or acetonitrile) with 0.5 molar equivalents of BAT-BM (N-{2-(N',N'-bis(2-maleimidoethyl)aminoethyl)}-$N^9$-(t-butoxycarbonyl)-$N^6$, $N^9$-bis(2-methyl-2-triphenylmethylthiopropyl)-6,9-diazanonanamide) pre-dissolved in acetonitrile or THF, at room temperature for approximately 1–18 h. The solution is then evaporated to dryness and (BAT-BS)-peptide conjugates deprotected by treatment with 10 mL TFA and 0.2 mL triethylsilane for 1 h. The solution is concentrated, the product adducts precipitated with ether, and then purified by HPLC.

Where appropriate, peptide precursors are cyclized (between the amino- and carboxyl-termini) by reaction of the sidechain-protected, N-terminal free amine and C-terminal free acid with diphenylphosphorylazide.

Sasrin™ resin-bound peptides are cleaved using a solution of 1% TFA in dichloromethane to yield the protected peptide. Where appropriate, protected peptide precursors are cyclized between the amino- and carboxyl-termini by reaction of sidechain-protected, amino-terminal free amine and carboxyl-terminal free acid using diphenylphosphorylazide.

HMP or Rink amide resin-bound products are routinely cleaved and protected cyclized peptides deprotected using a solution comprised of trifluoroacetic acid (TFA), or TFA and methylene chloride, optionally comprising water, thioanisole, ethanedithiol, and triethylsilane or triisopropylsilane in ratios of 100:5:5:2.5:2, for 0.5–3 hours at room temperature. Where appropriate, products were re-S-tritylated in triphenolmethanol/ TFA, and N-Boc groups re-introduced into the peptide using $(Boc)_2O$.

Crude peptides are purified by preparative high pressure liquid chromatography (HPLC) using a Waters Delta Pak C18 column and gradient elution using 0.1% trifluoroacetic acid (TFA) in water modified with acetonitrile. Acetonitrile is evaporated from the eluted fractions which are then lyophilized. The identity of each product is confirmed by fast atom bombardment mass spectroscopy (FABMS) or by electrospray mass spectroscopy (ESMS).

Receptor binding VIP peptides, derivatives and analogues synthesized as provided herein, as well as the products of such synthesis identified by FABMS, are shown in Table I below.

TABLE I

|  | Peptide | $M^+$ (ESMS) |
|---|---|---|
| P887 | HSDAVFTDNYTRLRKQMAVKKYLNSILN (ε-K)GC.amide | 3614 |
| P916 | HSDAVFTDNYTRLRKQMAVKKYLNSILNGGC. amide | 3557 |

TABLE I-continued

| Peptide | | M+ (ESMS) |
|---|---|---|
| P915 | AGCHSDAVFTDNYTRLRKQMAVKKYLNSILN. amide | 3543 |
| P917 | HSDAVFTDNYTRLRKQMAVKKYLNSILNC(BAT). amide | 3734 |

ESMS is electroscopy mass spectrometry.

EXAMPLE 3

A General Method for Radiolabeling with Tc-99m 0.1 mg of a peptide prepared as in Example 2 was dissolved in 0.1 mL or 0.2 mL of water or 0.9% saline. Tc-99m gluceptate was prepared by reconstituting a Gluscoscan vial (E.I. DuPont de Nemours, Inc., Wilmington, DE) with 0.25 mL of Tc-99m sodium pertechnetate containing up to 200 mCi and allowed to stand for 15 minutes at room temperature. 25 μl of Tc-99m gluceptate was then added to the peptide and the reaction allowed to proceed at room temperature for 15 or 55 min and then filtered through a 0.2 μm filter.

The Tc-99m labeled peptide purity was determined by reverse-phase HPLC using the following conditions: a Waters Delta Pak C-18, 5μ, 3.9 mm×150 mm analytical column was loaded with each radiolabeled peptide, and the peptides eluted at a solvent flow rate equal to 1 mL/min (Delta-Pak). Gradient elution was performed using a gradient of 20–50% Solvent B/Solvent A (Solvent A is 0.1% $CF_3COOH$ in water and Solvent B is 0.1% $CF_3COOH$ in 90/10 $CH_3CN/H_2O$) for 20 min., followed by 100% B/A for 3 min.

Radioactive components were detected using an in-line radiometric detector linked to an integrating recorder. Tc-99m gluceptate and Tc-99m sodium pertechnetate elute between 1 and 4 minutes under these conditions, whereas the Tc-99m labeled peptides eluted after a much greater amount of time. Peptides were detected by in-line spectrophotometric detection at 220 nm.

Non-radioactive rhenium complexes were prepared by co-dissolving each of the peptide reagents of the invention with about one molar equivalent of tetrabutylammonium oxotetrabromorhenate (+5), prepared as described by Cotton et al. (1966, Inorg. Chem. 5: 9–16) in dimethylformamide or acetonitrile/water and stirred for 0.5–5 days. The rhenium complexes were isolated by reverse phase HPLC as described above for Tc-99m labeled peptides and were characterized by FABMS or ESMS. Non-radioactive peptides were detected as peptides by in-line spectrophotometric detection at 220 nm.

Radioactive rhenium complexes, using for example Re-186 or Re-188, are prepared from the appropriate perrhenate salts using the same protocol as for Tc-99m labeling, or by adding a reducing agent to a solution of the peptide and perrhenate, or optionally using a ligand transfer agent such as citrate and incubating the reaction at a temperature between room temperature and 100° C. for between 5 and 60 min.

Results of HPLC purification of peptides, Tc-99m labeled peptides and ReO-complexed peptides are shown in Table II.

TABLE II

| | HPLC Retention Time (min.) | | |
|---|---|---|---|
| Peptide | Peptide | ReO-complex | Tc-99m Labeled |
| (VIP)-(ε-K)GC.amide | 11.6 | 12.7 | 12.9 |
| (VIP)-GGC.amide | 12.1 | 12.9 | 12.8 |
| AGC-(VIP).amide | 12.6 | 12.0 | 11.7 |
| (VIP)-C(BAT).amide | 13.8 | 17.9 | 18.4 | where VIP =HSDAVFTDNYTRLRKQMAVKKYLNSILN

EXAMPLE 4

Biological Assays

Peptides of the invention, or ReO-complexed embodiments thereof, were assayed for biological activity in competition binding assays with $^{125}$I-labeled VIP.

Such assays are performed in a standard assay of VIP binding, using membranes isolated from guinea pig lung; on peripheral blood monocytes and platelets; and on a variety of human tumor cell lines.

In the practice of these methods, VIP was radioiodinated using the iodogen method, as described in Schanen et al. (1991, Lancet 6: 395–396). Briefly, 50 μg VIP in 10 μL 0.5M phosphate buffer (pH 7.5), an appropriate amount of the radioisotope, and 6 μg iodogen were incubated to room temperature for about 30 min with gentle stirring. Radioiodinated VIP was purified from unincorporated radioiodine by HPLC chromatography, and dissolved in phosphate buffered saline (PBS) supplemented with 0.1% human serum albumin and 0.1% Tween-80 detergent.

In assays using isolated rat guinea pig lung membranes, lungs were obtained from male guinea pigs and membranes isolated essentially as described in Carstairs and Barnes (1986, J. Pharmacol. Exp. Ther. 239: 249–255, incorporated by reference). 0.2 mg of membrane preparation was incubated with 0.01 nM $^{125}$I-labeled VIP in the presence or absence of varying concentrations of the peptides of the invention or ReO complexes thereof. From a comparison of the extent of binding in the presence or absence of the unlabeled VIP compounds, a concentration was determined for each compound corresponding to inhibition of $^{125}$I-labeled VIP binding by 50% (termed the $IC_{50}$).

Using these procedures, results for each of the tested compounds are shown in Table IV. These results indicate that the peptides and ReO complexes of the peptide of the invention are potent inhibitors of VIP binding to VIP receptor-expressing lung membranes.

TABLE IV

| Peptide | ReO-Complexed Peptide | $IC_{50}$ (μM) | Remarks |
|---|---|---|---|
| P887 | | <0.01 | 68% inhibition @ 0.01 μM |
| P915 | | 0.05 | |
| P916 | | <0.01 | 79% inhibition @ 0.01 μM |
| P917 | | <0.01 | 83% inhibition @ 0.01 μM |
| | P887 | 0.02 | |
| | P915 | <0.01 | $0.001 < IC_{50} < 0.01$ μM |
| | P916 | 0.02 | |
| | P917 | 0.0069 | $K_i = 0.0067$ μM |

Similar experiments were performed using normal peripheral human platelets and mononuclear cells.

In these experiments, platelets are isolated according to the method of Virgolini et al. (1990, Brit. J. Cancer 12:

849–861). Peripheral mononuclear cells (PMNCs) are isolated from whole blood buffy coat by Ficoll density gradient centrifugation ($\rho=1.077$). Before assay, cells are washed in 50 mM Tris-HCl buffer, pH 7.5 and then resuspended in the same buffer supplemented with 5 mM $MgCl_2$, 1 mM $CaCl_2$ and 0.1M NaCl. About $5\times10^7$ cells per assay are used.

Results of these assays using platelets and PMNCs are shown in Table V, demonstrating that the ReO complexes of the peptides of the invention are potent antagonists to VIP receptor binding on these peripheral blood cells.

TABLE V

| Peptide | $IC_{50}$ (nM): Platelets | $IC_{50}$ (nM): PMNCs |
|---------|---------------------------|------------------------|
| VIP     | 4.0                       | 5.5                    |
| P887    | 6                         | 6.0                    |
| P915    | 4.5                       | 7.5                    |
| P916    | 3.0                       | 6.5                    |
| P917    | 0.8                       | 2.7                    | where VIP is HSDAVFTDNYTRLRKQMAVKKYLNSILN

The following tumor cell lines were assayed using the above-described binding competition assay: KU812 cells (human chronic myelogenous leukemia cell line); COLO320 cells (human colon adenocarcinoma cell line); HT29 cells (human colorecal adenocarcinoma cell line); PANC1 cells (human pancreatic adenocarcinoma cell line); HMC1 cells (human mast cells). Each cell line is assayed essentially as described above for human peripheral blood cells. Cells are grown in RPMI media or Dulbecco's Modified Media (HMC1 cells) supplemented with 10% fetal calf serum, glutamine and antibiotics using standard cell culture techniques (see *Animal Cell Culture: A Pratical Approach*, Freshney, ed, IRL Press: Oxford, UK, 1992).

Results of these assays are shown in Table VI, demonstrating that the ReO complexes of the peptides of the invention are potent inhibitors of VIP binding to these human tumor cells.

TABLE VI

| | $IC_{50}$ (nM): | | | | |
|---|---|---|---|---|---|
| Peptide | KU812 | COLO320 | HT29 | PANC1 | HMC1 |
| VIP  | 0.8  | 1.5 | 1.2 | 4.2  | 7   |
| P887 | 5.2  | 6.0 | 6.6 | >10  | 8.5 |
| P915 | N.D. | 6.7 | 7.0 | 14   | 15  |
| P916 | N.D. | 4.0 | 8.5 | 12.5 | 7   |
| P917 | 1.0  | 2.0 | 2.2 | 3.7  | 7   | where VIP is HSDAVFTDNYTRLRKQMAVKKYLNSIL-N.amide

These results demonstrate that the VIP peptides and ReO complexes thereof provided by the invention are capable of specifically binding to VIP receptors in standard in vitro assays on a variety of normal and human tumor cell types. These results indicate that the VIP peptides of the invention have utility as scintigraphic imaging agents for imaging tumor sites in humans.

These assays are used to select effective radiotherapeutic agents as provided by the invention, wherein the in vitro VIP receptor-expressing cells and membranes are used to detect and quantify VIP receptor binding of Re-complexed reagents of the invention comprising VIP peptides covalently linked to a chelating moiety incorporated into the reagent during peptide synthesis. Such Re-complexed reagents can then be evaluated in competition binding assays as described herein using radioiodinated VIP.

It should be understood that the foregoing disclosure emphasizes certain specific embodiments of the invention and that all modifications or alternatives equivalent thereto are within the spirit and scope of the invention as set forth in the appended claims.

We claim:

1. A reagent for preparing a radiopharmaceutical, comprising a synthetic, receptor-binding vasoactive intestinal peptide (VIP) covalently linked to a technetium or rhenium chelating moiety, wherein said chelating moiety is incorporated into the reagent during synthesis of the peptide, and wherein the radiopharmaceutical when labeled with technetium or rhenium has a VIP receptor binding affinity that is not less than about one-tenth the affinity of radioiodinated native VIP for said receptor.

2. A scintigraphic imaging agent comprising the reagent of claim 1 radiolabeled with technetium-99m.

3. A radiotherapeutic agent comprising the reagent of claim 1 radiolabeled with a cytotoxic radioisotope selected from the group consisting of rhenium-186 and rhenium-188.

4. A kit for preparing a radiopharmaceutical preparation, said kit comprising a sealed vial containing a predetermined quantity of the reagent of claim 1 and a sufficient amount of a reducing agent to label the reagent with technetium-99m, rhenium-186 or rhenium-188.

5. The reagent according to claim 1, produced by in vitro chemical synthesis.

6. The reagent according to claim 5 produced by solid phase peptide synthesis.

7. The reagent of claim 1 wherein the chelating moiety has a formula selected from the group consisting of:

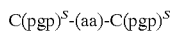

I.

wherein $(pgp)^S$ is H or a thiol protecting group and (aa) is a primary α- or β-amino acid;

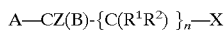

II.

wherein

A is H, HOOC, H$_2$NOC, (amino acid or peptide)13 NHOC, (amino acid or peptide)—OOC or $R^4$;

B is H, SH, —NHR$^3$, —N(R$^3$)-(amino acid or peptide), or $R^4$;

X is H, SH, —NHR$^3$, —N(R$^3$)-(amino acid or peptide) or $R^4$;

Z is H or $R^4$;

$R^1$, $R^2$, $R^3$ and $R^4$ are independently H or lower straight or branched chain or cyclic alkyl;

n is 0, 1 or 2;

(peptide) is a peptide of 2 to about 10 amino acids; and where B is —NHR$^3$ or —N(R$^3$)-(amino acid or peptide), X is SH, and n is 1 or 2;

where X is —NHR$^3$ or —N(R$^3$)-(amino acid or peptide), B is SH, and n is 1 or 2;

where B is H or $R^4$, A is HOOC, H$_2$NOC, (amino acid or peptide)—NHOC, (amino acid or peptide)—OOC, X is SH, and n is 0 or 1;

where A is H or $R^4$, then where B is SH, X is —NHR$^3$ or —N(R$^3$)-(amino acid or peptide) and where X is SH, B is —NHR$^3$ or —N(R$^3$)-(amino acid or peptide) and n is 1 or 2;

where X is H or $R^4$, A is HOOC, H$_2$NOC, (amino acid or peptide)-NHOC, (amino acid or peptide)—OOC and B is SH;

where Z is methyl, X is methyl, A is HOOC, H$_2$NOC, (amino acid or peptide)—NHOC, (amino acid or peptide)—OOC, B is SH and n is 0; and wherein the thiol moiety is in the reduced form and (amino acid) is any primary α- or β-amino acid not containing a thiol group;

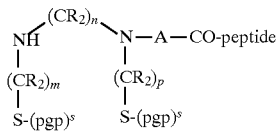

III.

wherein each R is independently H, CH$_3$ or C$_2$H$_5$;

each $(pgp)^S$ is independently a thiol protecting group or H;

m, n and p are independently 2 or 3;

A=linear or cyclic lower alkyl, aryl, heterocyclyl, combinations or substituted derivatives thereof;

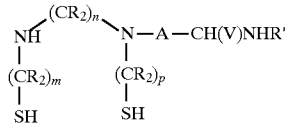

IV.

wherein each R is independently H, CH$_3$ or C$_2$H$_5$;

m, n and p are independently 2 or 3;

A=linear or cyclic lower alkyl, aryl, heterocyclyl, combinations or substituted derivatives thereof;

V=H or —CO-peptide;

R'=H or peptide;

and wherein when V=H, R'=peptide and when R'=H, V=—CO-peptide;

wherein each R is independently H, lower alkyl having 1 to 6 carbon atoms, phenyl, or phenyl substituted with lower alkyl or lower alkoxy, and wherein each n is independently 1 or 2;

a monoamine, diamide, monothiol group having a formula:

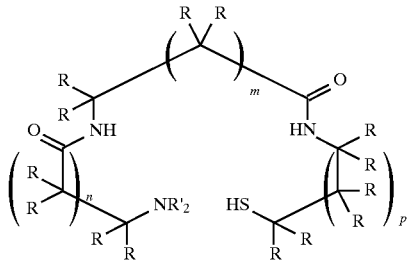

wherein:

n, m and p are each independently 0 or 1, each R'is independently H, lower alkyl, hydroxyalkyl (C$_2$–C$_4$), or alkoxyalkyl (C$_2$–C$_4$);

each R is independently H or R", where R"is substituted or unsubstituted lower alkyl or phenyl not comprising a thiol group;

one R or R'is L, wherein when an R'is L, —NR'$_2$ is an amnine; and

L is a bivalent linking group linking the radiolabel binding moiety to the peptide;

and a monoamine, diamide, monothiol group having a formula:

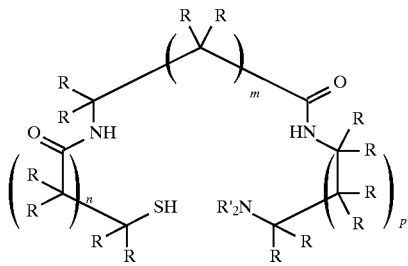

wherein:

n, m and p are each independently 0 or 1, each R'is independently H, lower alkyl, hydroxyalkyl ($C_2$–$C_4$), or alkoxyalkyl ($C_2$–$C_4$);

each R is independently H or R", where R"is substituted or unsubstituted lower alkyl or phenyl not comprising a thiol group;

one R or R'is L, wherein when an R'is L, —NR'$_2$ is an amine; and

L is a bivalent linking group linking the radiolabel binding moiety to the peptide.

8. The reagent of claim 7, wherein the chelating moiety has formula I and (pgp)$^S$ has a formula

—CH$_2$—NH—CO—R wherein R is a lower alkyl having 1 to 6 carbon atoms, a 2-pyridyl, a 3-pyridyl, a 4-pyridyl, a phenyl, or a phenyl substituted with a lower alkyl, a hydroxy, a lower alkoxy, a carboxy, or a lower alkoxycarbonyl.

9. The reagent of claim 8, wherein the chelating moiety has the formula:

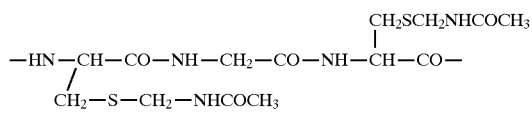

10. The reagent of claim 7 wherein chelating moiety is selected from the group consisting of:

IIa. -(amino acid)$^1$-(amino acid)$^2$—{A—CZ(B)—{C(R$^1$R$^2$)}$_n$—X},

IIb. —{A—CZ(B)—{C(R$^1$R$^2$)}$_n$—X}-(amino acid)$^1$-(amino acid)$^2$,

IIc. -(a primary α,β- or β,γ-diamino acid)-(amino acid)$^1$-{—A—CZ(B)—{C(R$^1$R$^2$)}$_n$-X}, and IId. —{A—CZ(B)—{C(R$^1$R$^2$)}$_n$—X}-(amino acid)$^1$-(a primary α,β- or β,γ-diamino acid)

wherein (amino acid)$^1$ and (amino acid)$^2$ are each independently any naturally-ocurring, modified, substituted or altered α- or β-amino acid not containing a thio, group;

A is H, HOOC, H$_2$NOC, (amino acid or peptide)—NHOC, (amino acid or peptide)—OOC or R$^4$;

B is H, SH or —NHR$^3$, —N(R$^3$)-(amino acid or peptide) or R$^4$;

X is SH or —NHR3, —N(R$^3$)-(amino acid or peptide) or R$^4$;

Z is H or R$^4$:

R$^1$, R$^2$, R$^3$ and R$^4$ are independently H or straight or branched chain or cyclic lower alkyl;

(peptide) is a peptide of 2 to about 10 amino acids;

n is an integer that is either 0, 1 or 2; and where B is —NHR$^3$ or —N(R$^3$)-(amino acid or peptide), X is SH and n is 1 or 2;

where X is —NHR$^3$ or —N(R$^3$)-(amino acid or peptide), B is SH and n is 1 or 2;

where B is H or R$^4$, A is HOOC, H$_2$NOC, (amino acid or peptide)—NHOC, (amino acid or peptide)—OOC, X is SH and n is 0 or 1;

where A is H or R$^4$, then where B is SH, X is —NHR$^3$ or —N(R$^3$)-(amino acid or peptide) and where X is SH, B is —NHR$^3$ or —N(R$^3$)-(amino acid or peptide) and n is 1 or 2;

where X is H or R$^4$, A is HOOC, H$_2$NOC, (amino acid or peptide)—NHOC, (amino acid or peptide)—OOC and B is SH;

where Z is methyl, X is methyl, A is HOOC, H$_2$NOC, (amino acid or peptide)—NHOC, (peptide)—OOC and B is SH and n is 0;

and wherein the thiol moiety is in the reduced form.

11. The reagent of claim 7 wherein the monoamine, diamide, monothiol chelating moiety comprising the reagent has the formula:

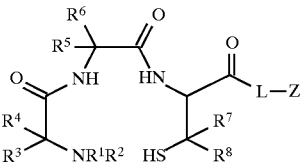

wherein:

R$^1$ and R$^2$ are each independently H, lower alkyl, hydroxyalkyl ($C_2$–$C_4$) or alkoxyalkyl ($C_2$–$C_4$);

R$^3$, R$^4$, R$^5$, and R$^6$ are independently H, substituted or unsubstituted lower alkyl or phenyl not comprising a thiol group;

R$^7$ and R$^8$ are each independently H, lower alkyl, lower hydroxyalkyl or lower alkoxyalkyl;

L is a bivalent linking moiety; and

Z is a peptide.

12. The reagent of claim 7 wherein the monoamine diamide, monothiol chelating moiety has the formula:

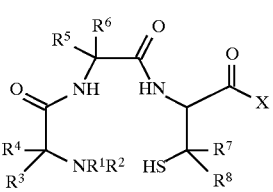

wherein:

R$^1$ and R$^2$ are each independently H, lower alkyl, hydroxyalkyl ($C_2$–$C_4$), or alkoxyalkyl ($C_2$–$C_4$);

R$^3$, R$^4$, R$^5$, and R$^6$ are independently H, substituted or unsubstituted lower alkyl or phenyl not comprising a thiol group and one of R$^3$, R$^4$, R$^5$, and R$^6$ is Z—L—(CR$_2$)$_n$—, where n is an integer from 1 to 6 and each R is , independently H, lower alkyl, or substituted lower alkyl;

R$^7$ and R$^8$ are each independently H, lower alkyl, lower hydroxyalkyl or lower alkoxyalkyl;

L is a bivalent liking moiety;

Z is a peptide; and

X is —NH$_2$,—NR$^1$R$^2$, or —NR$^1$—Y, where Y is an amino acid, an amino acid amide, or a peptide of from 2 to about 20 amino acids.

13. The reagent of claim 7 wherein the monoamine, diamide, monothiol chelating moiety has the formula:

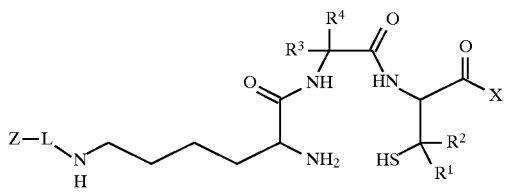

wherein;
R¹ and R² are each independently H, lower alkyl, hydroxyalkyl (C₂–C₄) or alkoxyalkyl (C₂–C₄);
R³, R⁴, R⁵, and R⁶ independently H, substituted or unsubstituted lower allyl or phenyl not comprising a thiol group;
X is —NH₂, —NR¹R²,or —NR¹—Y, where Y is an amino acid, an amino acid amide, or a peptide having from 2 to about 20 amino acids;
n is an integer from 1 to 6;
L is a bivalent linking moiety; and
Z is a peptide.

14. The reagent of claim 7 wherein the monoamine, diamide, monothiol chelating moiety comprising the reagent has the formula:

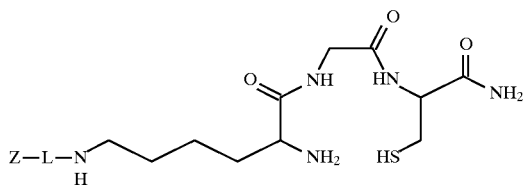

wherein:
L is a linker group; and
Z is a peptide.

15. The reagent of claim 1 wherein the chelating moiety is selected from the group consisting of:
(amino acid)¹-(amino acid)²-cysteine-,
(amino acid)¹-(amino acid)²-isocysteine-,
(amino acid)¹-(amino acid)²-homocysteine-,
(amino acid)¹-(amino acid)²-penicillamine-,
(amino acid)¹-(amino acid)²-2-mercaptoethylamine-,
(amino acid)¹-(amino acid)²-2-mercaptopropylamine-,
(amino acid)¹-(amino acid)²-2-mercapto-2-methylpropylamine-,
(amino acid)¹-(amino acid)²-3-mercaptopropylamine-,
wherein:
(amino acid) is a primary α- or β-amino acid not comprising a thiol, and wherein the chelating moiety is attached to the peptide via a covalent bond with the carboxyl terminus of the chelating moiety or a side chain on one of the amino acid groups comprising the chelating moiety.

16. The reagent of claim 15 wherein (amino acid)¹ is either a α,ω- or β,ω-diamino acid wherein the α- or β-amine is a free amine.

17. The reagent of claim 7 wherein the chelating moiety is selected form the group consisting of:
-cysteine-(amino acid)-(α,β- or β,γ-diamino acid);
-isocysteine-(amino acid)-(α,β- or β,γ-diamino acid);
-homocysteine-(amino acid)-(α,β- or β,γ-diamino acid);
-penicillamine-(amino acid)-(α,β- or β,γ-diamino acid);
2-mercaptoacetic acid-(amino acid)-(α,β- or β,γ-diamino acid);
2- or 3-mercaptopropionic acid-(amino acid)-(α,β- or β,γ-diamino acid);
2-mercapto-2-methylpropionic acid-(amino acid)-(α,β- or β,γ-diamino acid);
wherein:
(amino acid) is a primary α- or β-amino acid not comprising a thiol; and wherein the chelating moiety is attached to the peptide via a covalent bond with the amino terminus of the chelating moiety or a side chain of one of the amino acid groups comprising the chelating moiety.

18. The reagent of claim 1 wherein the chelating moiety has a formula selected from the group consisting of:
Gly-Gly-Cys-
Ala-Gly-Cys-
-(ε-Lys)-Gly-Cys-
-(δ-Orn)-Gly-Cys-
-(γ-Dab)-Gly-Cys-
-(β-Dap)-Gly-Cys-
and
-Cys(BAT).

19. A scintigraphic imaging agent comprising the reagent of claim 7 radiolabeled with technetium-99m.

20. A radiotherapeutic agent comprising the reagent of claim 7 and a cytotoxic radioisotope selected from the group consisting of rhenium-186 and rhenium-188.

21. A kit for preparing a radiopharmaceutical preparation, said kit comprising a sealed vial containing a predetermined quantity of the reagent of claim 7 and a sufficient amount of a reducing agent to label the reagent with technetium-99m, rhenium-186 or rhenium-188.

22. A method of radiotherapy for an animal suffering a VIP-related disease, comprising the step of administering an effective therapeutic amount of the agent of claim 20 to the animal.

23. The reagent according to claim 7, produced by in vitro peptide synthesis.

24. The reagent according to claim 23 produced by solid phase peptide synthesis.

25. A method of making the reagent of claim 1, wherein the chelating moiety is incorporated into the reagent at a known position of the peptide.

26. A composition of matter selected from the group consisting of:
HSDAVFTDNYTRLRKQMAVKKYLNSILN(ε-K)GC.amide
HSDAVFTDNYTRLRKQMAVKKYLNSIL-NGGC.amide (SEQ ID No. 2)
AGCHSDAVFTDNYTRLRKQMAVKKYLN-SILN.amide (SEQ ID No. 3)
and
HSDAVFTDNYTRLRKQMAVKKYLNSILNC(BAT).amide (SEQ ID No. 4).

27. The composition of matter of claim 24, further comprising technetium-99m.

28. The composition of matter of claim 24, further comprising rhenium-186 or rhenium- 188.

29. A reagent according to claim 1, wherein the chelating moiety is incorporated into the peptide at the carboxyl terminus of the peptide.

30. A reagent according to claim 7, wherein the chelating moiety is incorporated into the peptide at the carboxyl terminus of the peptide.

31. A vasoactive intestinal peptide (VIP) reagent for preparing a radiopharmaceutical, comprising
   (a) at least two synthetic, VIP receptor-binding peptides;
   (b) at least two technetium or rhenium chelating moieties, wherein said chelating moieties are incorporated into the reagent during synthesis of the reagent, and
   (c) a polyvalent linker covalently linked to the peptides and to the chelating moieties, thereby forming a multimeric reagent;
wherein
   (i) said reagent has a molecular weight of less than about 20,000 daltons; and
   (ii) the radiopharmaceutical when labeled with technetium or rhenium has a VIP receptor binding affinity that is not less than about one-tenth the affinity of radioiodinated native VIP for said receptor.

32. The reagent of claim 1, wherein the peptide has an amino acid sequence
   -SDAVFTDNYTRLRKQMAVKKYLNSILN.amide (SEQ ID NO:5)
and wherein the chelating moiety is incorporated into the reagent at a sidechain of an amino acid in said sequence or at a carboxyl terminus of the peptide.

33. The reagent of claim 7, wherein the peptide has an amino acid sequence
   -SDAVFTDNYTRLRKQMAVKKYLNSILN.amnide (SEQ ID NO:5)
and wherein the chelating moiety is incorporated into the reagent at a sidechain of an amino acid in said sequence or at a carboxyl terminus of the peptide.

34. The reagent of claim 1, wherein the peptide has an amino acid sequence
   -NYTRLRKQMAVKKYLNSILN.amide (SEQ ID NO:6)
and wherein the chelating moiety is incorporated into the reagent at a sidechain of an amino acid in said sequence or at a carboxyl terminus of the peptide.

35. The reagent of claim 7, wherein the peptide has an amino acid sequence
   -NYTRLRKQMAVKKYLNSILN.amide (SEQ ID NO:6)
and wherein the chelating moiety is incorporated into the reagent at a sidechain of an amino acid in said sequence or at a carboxyl terminus of the peptide.

36. The reagent of claim 1, wherein the peptide has an amino acid sequence
   -KQMAVKKYLNSILN.amide (SEQ ID NO:7)
and wherein the chelating moiety is incorporated into the reagent at a sidechain of an amino acid in said sequence or at a carboxyl terminus of the peptide.

37. The reagent of claim 7, wherein the peptide has an amino acid sequence
   -KQMAVKKYLNSILN.amide (SEQ ID NO:7)
and wherein the chelating moiety is incorporated into the reagent at a sidechain of an amino acid in said sequence or at a carboxyl terminus of the peptide.

* * * * *